US012104166B2

(12) United States Patent
Maguire

(10) Patent No.: US 12,104,166 B2
(45) Date of Patent: Oct. 1, 2024

(54) PAYLOAD DELIVERY ACROSS CELL MEMBRANES USING CONTINUOUS FLOW FLUIDIC SYSTEM

(71) Applicant: Avectas Limited, Kildare (IE)

(72) Inventor: Michael Maguire, Dublin (IE)

(73) Assignee: Avectas Limited, Kildare (IE)

( * ) Notice: Subject to any disclaimer, the term of this patent is extended or adjusted under 35 U.S.C. 154(b) by 832 days.

(21) Appl. No.: 16/631,346

(22) PCT Filed: Jul. 18, 2018

(86) PCT No.: PCT/IB2018/000909
§ 371 (c)(1),
(2) Date: Jan. 15, 2020

(87) PCT Pub. No.: WO2019/016600
PCT Pub. Date: Jan. 24, 2019

(65) Prior Publication Data
US 2020/0216862 A1    Jul. 9, 2020

Related U.S. Application Data

(60) Provisional application No. 62/533,825, filed on Jul. 18, 2017.

(51) Int. Cl.
*C12N 15/87*    (2006.01)
*B01L 3/00*    (2006.01)
*C12N 5/0783*    (2010.01)

(52) U.S. Cl.
CPC ........ *C12N 15/87* (2013.01); *B01L 3/502761* (2013.01); *C12N 5/0636* (2013.01);
(Continued)

(58) Field of Classification Search
None
See application file for complete search history.

(56) References Cited

U.S. PATENT DOCUMENTS 6,165,977 A * 12/2000 Mochly-Rosen .... C12N 9/1205
514/17.7
7,999,937 B1    8/2011 Srivastava et al.
(Continued)

FOREIGN PATENT DOCUMENTS

WO    2012175918 A1    12/2012

OTHER PUBLICATIONS

PCT Search Report and Written Opinion issued in connection with corresponding PCT Application No. PCT/IB2018/000909 on Mar. 14, 2019.

*Primary Examiner* — Matthew D Krcha
(74) *Attorney, Agent, or Firm* — Mintz Levin Cohn Ferris Glovsky and Popeo, P.C.

(57) ABSTRACT

Methods, systems, processes, and apparatuses are provided for delivery across cell membranes. In one aspect, an apparatus includes a substrate including a mixing channel, a process chamber, and a dilution channel to perform delivery of the payload to across the cell membranes. In another aspect, a system includes reservoirs for a cell suspension, a delivery solution, and a stop solution connected to a pump. The system further includes an agitator, a heater, a temperature controller, and a controller to operate the system. In yet another aspect, cells in suspension are mixed with a delivery solution in a microfluidic mixing chip. The delivery solution includes a permeabilization agent to cause permeabilization of the cells, allowing delivery of a payload from the delivery solution to the cells across the cell membranes.

23 Claims, 18 Drawing Sheets

(52) U.S. Cl.
CPC .................. *B01L 2200/0652* (2013.01); *B01L 2300/0627* (2013.01); *B01L 2300/0861* (2013.01); *B01L 2300/0883* (2013.01); *B01L 2300/12* (2013.01); *B01L 2300/1805* (2013.01); *B01L 2400/0439* (2013.01)

(56) References Cited

U.S. PATENT DOCUMENTS

| | | | |
|---|---|---|---|
| 2004/0072288 A1* | 4/2004 | Collas | C12N 5/0636 |
| | | | 435/372 |
| 2009/0325217 A1 | 12/2009 | Luscher | |
| 2011/0038836 A1* | 2/2011 | Cooper | A61P 7/00 |
| | | | 424/93.2 |
| 2013/0171628 A1* | 7/2013 | Di Carlo | C12M 29/00 |
| | | | 435/7.1 |
| 2013/0315937 A1* | 11/2013 | Lee | A61K 9/127 |
| | | | 424/179.1 |
| 2014/0377145 A1* | 12/2014 | Govyadinov | B01L 3/502715 |
| | | | 422/505 |
| 2016/0348073 A1* | 12/2016 | Meissner | C12N 15/85 |

* cited by examiner (a)

(b)

(c)

(a)

(b)

PAYLOAD DELIVERY ACROSS CELL MEMBRANES USING CONTINUOUS FLOW FLUIDIC SYSTEM

CROSS-REFERENCES TO RELATED APPLICATIONS

This application is a national stage application filed under 35 U.S.C. § 371, of International Patent Application No. PCT/IB2018/000909 filed Jul. 18, 2018, which claims the benefit of and priority under 35 U.S.C. § 119(e) to U.S. Provisional Application No. 62/533,825 filed on Jul. 18, 2017, the entire contents of each of which are hereby expressly incorporated herein by reference.

TECHNICAL FIELD

The subject matter described herein relates to delivery of payloads across cell membranes.

BACKGROUND

Despite some advances, delivery of certain particles and/or molecules into cells remains a challenge. For example, factors such as size or charge of a molecule to be delivered into a cell can limit and/or prevent delivery of the molecule into the cell. Delivery across a cell membrane can be complicated by the molecule and/or the membrane of the cell. A plasma or cell membrane is a semi-permeable biological membrane, which acts as a selective barrier. The membrane regulates an internal chemical composition of the cell. As the selective barrier for the cell, the membrane only allows certain molecules to passively translocate across the membrane through, for example, passive diffusion into the cell. Small, hydrophobic molecules (such as $O_2$, $CO_2$, and $N_2$) and small, uncharged polar molecules (such as $H_2O$ and glycerol) can passively diffuse across cell membranes. Larger, uncharged polar molecules (such as amino acids, glucose, and nucleotides) and ions (such as $H^+$, $Na^+$, $K^+$ and $Cl^-$) cannot passively diffuse across cell membranes.

SUMMARY

The current subject matter provides a cell engineering method and platform to deliver compounds or mixtures of compounds (e.g., payload) into cells across cell membranes by contacting the cells with a delivery solution containing the payload and an agent that reversibly permeates or dissolves a cell membrane. In particular, by continuously supplying the cells in a suspension and the delivery solution into a system in which the suspension and the solution are mixed, the cells are permeabilized, and the payload is delivered across the permeabilized cell membranes. Methods, systems, processes, and devices for use in delivery across cell membranes are provided.

Batch processes in the related arts to perform intercellular delivery can process finite number of cells (from 1 to $10^8$ or $10^9$) per each batch, but can be difficult to scale up to process a higher cell loading. Conversely, some implementations of the current subject matter relates to delivery technology that can facilitate a continuous flow delivery of a broad range of payloads to cells. Compared to batch processes, the continuous flow platform can enable a steady-state process in which the concentrations of the cells, payloads and permeabilization agents can be maintained in a steady-state over the entire process duration. Moreover, the system can be implemented as a closed system and enable sterile transfection, which makes the system and the method suitable for therapeutic applications. Accordingly, some implementations the continuous flow platform can provide better consistency throughout the operation, yield a high throughput to cover the therapeutic capacity range, and possess a better scale-up potential.

In an aspect, a device to perform payload delivery across cell membranes is provided. The device can include a substrate that includes a first fluidic channel including a first inlet configured to receive a population of cells in a suspension, a second fluidic channel including a second inlet configured to receive a delivery payload in a delivery solution, a mixing channel that connects the first and the second fluidic channels. The mixing channel can cause the first and the second fluidic channels to be in fluidic communication and can mix the suspension and the delivery solution. The substrate of the device can further include a process chamber connected to the mixing channel configured to retain the mixture of the suspension and the delivery solution for a period of time for exposing the population of cells to the delivery solution. A third fluidic channel including a third inlet can also be included in the substrate to receive a stop solution, and a dilution channel can be provided to be connected to the process chamber and to the third fluidic channel. The dilution channel can combine and output fluid of the process chamber with the stop solution supplied from the third fluidic channel. The substrate of the device can further include a separator connected to the dilution channel for separating transformed cells and a waste stream. Moreover, the device can include a fourth fluidic channel including a fourth inlet configured to receive one or more additive streams.

One or more of the following features can be included in any feasible combination. The process chamber can include one or more diagnostic ports for measuring a temperature and a pressure in the process chamber and/or for extracting a sample. The substrate can include an optically opaque material and an optically transparent material that forms an optical window. The optical window is arranged for imaging of cells within at least one of the first channel, the mixing channel, the process chamber, and/or the dilution channel.

In some implementations, the process chamber can be sized and shaped to control an exposure time of the population of cells to the delivery solution. For example, a length of the process chamber can be chosen to control the residence time of the mixture of cells and delivery solution before the mixture is diluted by the stop solution.

In embodiments, the mixing channel can have geometries including a herringbone pattern, an interdigitated pattern, and/or a double T pattern for mixing. The process chamber can have geometries including a straight channel, a serpentine channel, a circular channel, and/or a plenum. The fluidic channels of the device can have channel widths within a range of 0.01 µm and 100 µm, for example, 0.01 µm, 0.05 µm, 0.1 µm, 0.5 µm, 1 µm, 5 µm, 10 µm, 20 µm, 30 µm, 40 µm, 50 µm, 60 µm, 70 µm, 80 µm, 90 µm or 100 µm. The channel widths can also be within a range of 100 µm and 1 mm, for example, 100 µm, 200 µm, 300 µm, 400 µm, 500 µm, 600 µm, 700 µm, 800 µm, 900 µm or 1 mm, or alternatively, a range that is greater than or equal to 1 mm, for example, 1 mm, 2 mm, 3 mm, 4 mm or 5 mm. The substrate of the device can be made of a material including silicon, silicon oxide, silicon carbide, silicon nitride, silicate glass, borosilicate glass, quartz, sapphire, polydimethylsiloxane (PDMS), polyethylene, polypropylene, polyurethane, polytetrafluoroethylene (PTFE), polyether ether ketone (PEEK) and/or stainless steel such as a steel alloy with at least 10.5% chromium content by mass. The stainless steel can include chromium-manganese-nickel alloys, chromium-nickel alloys, or the like. The stainless steel can include, for example, 304 grade stainless steel or 316 grade stainless steel. The first inlet, the second inlet, the third inlet, and a downstream end of the dilution channel can be configured to be in closed fluidic communication.

In another aspect, a system to perform payload delivery across cell membranes is provided. The system can include the device described above, and further include a cell suspension reservoir connected to the first inlet of the first fluidic channel, a delivery solution reservoir connected to the second inlet of the second fluidic channel, a stop solution reservoir connected to the third inlet of the third fluidic channel, at least one pump configured to supply fluids in the reservoirs to the respective inlets, and a controller connected to the pump and configured to adjust flow rates of the fluids. The system can further include an agitator configured to vibrate at least one of the mixing channel, the process chamber, or the dilution channel. The agitator can include a low frequency pressure pulse generator, an ultrasonic vibrator, and/or a mechanical vibrator. The system can further include a heater and a temperature controller, which are configured to maintain or adjust a temperature of at least one of the mixing channel, the process chamber, or the dilution channel. The heater and the temperature controller can include multiple heating zones.

The delivery solution can include an isotonic aqueous solution, the aqueous solution including the payload and an alcohol at 2-5% or greater than or equal to 5% concentration by volume. The alcohol comprises ethanol. The aqueous solution can include greater than 10% ethanol. The aqueous solution can include between 20-30% ethanol, for example, 20%, 21%, 22%, 23%, 24%, 25%, 26%, 27%, 28%, 29% or 30%. The aqueous solution can include 27% ethanol. The aqueous solution can include between 12.5-500 mM KCl (potassium chloride), for example, 12.5 mM, 25 mM, 50 mM, 75 mM, 100 mM, 150 mM, 200 mM, 250 mM, 300 mM, 350 mM, 400 mM, 450 mM or 500 mM. The aqueous solution can include between 106 mM KCl.

The system can further include the filter plate, the well can be configured to contain a population of non-adherent cells. The non-adherent cell can include a peripheral blood mononuclear cell. The non-adherent cell can include an immune cell. The non-adherent cell can include a T lymphocyte. The payload can include a messenger ribonucleic acid (mRNA). The mRNA can encode a gene-editing composition. The gene editing composition can reduce the expression of PD-1 (programmed cell death protein 1). The mRNA can encode a chimeric antigen receptor. The current subject matter can be for use to deliver a cargo compound or composition to a mammalian cell.

In yet another aspect, a method of delivery across a cell membrane is provided that includes mixing a population of cells in a suspension and a delivery payload in a delivery solution. The delivery solution causes the population of cells to experience permeabilization and the delivery payload is delivered across membranes of the population of cells.

The method can vary in numerous ways. For example, the population of cells can include T cells and the delivery payload can include a nucleic acid, e.g., a mRNA, a protein, as well as a mixture or complex of a protein and a nucleic acid. In another example, the delivery solution can include alcohol. The suspension and the delivery solution can experience a first mixing cascade and a second mixing cascade. In one example, mixing the population of cells and the delivery payload can include pumping the population of cells and the delivery payload into a microfluidic mixing chip. A narrowest channel of the microfluidic mixing chip can be of a diameter that is larger than the diameter of a cell in the cell suspension, e.g., at least 5 times larger than diameters of the population of cells. In another example, the method can include introducing a stop solution to the population of cells and the delivery payload subsequent to mixing the population of cells and the delivery payload such that the stop solution causes the population of cells to stop experiencing permeabilization or experience a reduction in permeabilization. Introducing the stop solution can also include providing a user-determined process delay before introducing the stop solution to the population of cells and the delivery payload. In another example, the population of cells and the delivery payload can experience laminar flows. The method can also include mixing at least one additive with the population of cells in the suspension and the delivery payload in the delivery solution.

In another aspect, a method of delivering a payload across a cell membrane is provided that includes introducing a population of cells and a delivery solution into a microfluidic mixing chip such that the population of cells and the delivery solution mix. Interaction between the population of cells and the delivery solution causes transfer of a delivery payload from the delivery solution to the population of cells across membranes of the population of cells.

The method can vary in numerous ways. For example, interaction between the population of cells and the delivery solution can cause permeabilization of the population of cells. The delivery solution can include alcohol, the population of cells can include T cells, and the delivery payload can include mRNA. In another example, the microfluidic mixing chip can cause the population of cells and the delivery solution experience a first mixing cascade and a second mixing cascade. In other examples, the method can include introducing a stop solution to the population of cells and the delivery solution subsequent to transfer of the payload across the membranes of the population of cells. The stop solution decreases or stops cell membrane permeabilization and can therefore reduce or prevent any additional transfers of payload across the membranes of the population of cells. The population of cells and the delivery solution can also experience laminar flows. In other examples, channels in the microfluidic mixing chip can be configured to optimize transfer of the payload from the delivery solution to the population of cells.

BRIEF DESCRIPTION OF THE DRAWINGS

The current subject matter will be more fully understood from the following detailed description taken in conjunction with the accompanying drawings, in which.

DETAILED DESCRIPTION

Figure 1:
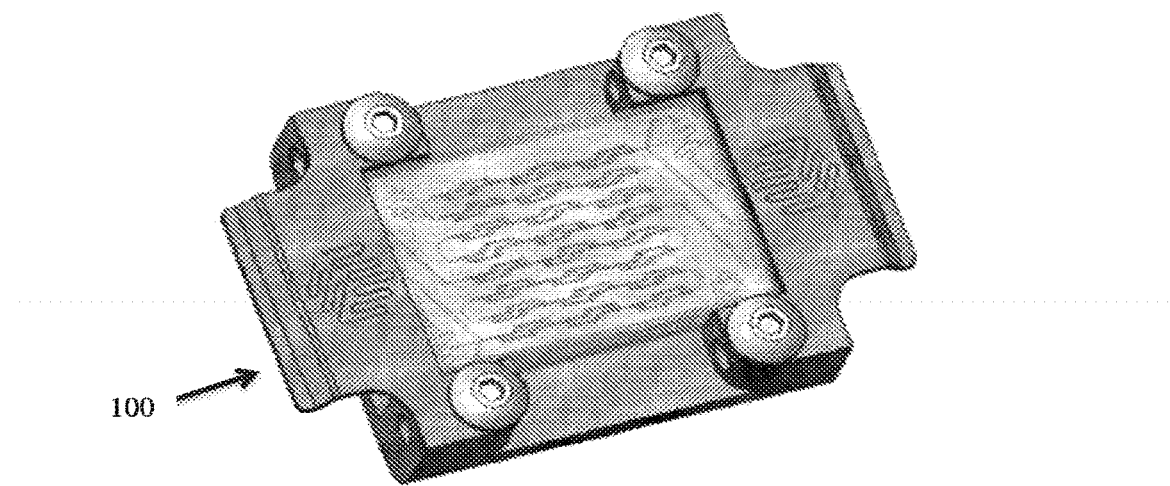
FIG. 1 is a proximal view of an embodiment of a microfluidic mixing chip.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Delivery of molecules into living cells is highly desirable for a wide range of applications. Generally, the types of molecules involved can be categorized according to the mass of the molecule: (i) small chemical molecules generally have an average molecular weight of: <1,000 Da; (ii) peptides generally have an average molecular weight of: ~5,000 Da; (iii) small RNA molecules generally have an average molecular weight of: ~15,000 Da; (iv) antibodies generally have an average molecular weight of: ~150,000 Da; and (v) nucleic acids, such as DNA, generally have an average molecular weight of: ~5,000,000 Da. Further details can be found in International Application No. PCT/US2015/057247, filed on Oct. 23, 2015 and expressly incorporated herein.

A variety of approaches are taken to deliver molecules across a plasma membrane and into a cell, each approach depending on the size and chemistry of molecule to be delivered. Organic solvents, such as Dimethyl sulfoxide (DMSO), have been used to deliver small chemical molecules. While the molecular basis of the action of DMSO on a plasma membrane is still obscure, DMSO is known to exhibit three distinct modes of action, each over a different concentration range. At low concentrations, DMSO induces plasma membrane thinning and increases fluidity of the hydrophobic core of the plasma membrane. At higher concentrations, DMSO induces transient water pores in the plasma membrane. At still higher concentrations, individual lipid molecules are irreversibly desorbed from the plasma membrane followed by a detrimental disintegration of the bilayer structure of the plasma membrane.

Introduction of larger, biological molecules such as oligopeptides, polypeptides or proteins, and nucleic acids (such as plasmid DNA, oligonucleotides, and siRNA) is referred to as 'transfection'. Use of traditional delivery compositions, such as DMSO, are not efficient for delivery of these larger molecules. siRNA molecules are usually delivered by liposome-mediated transfection (lipofection). Plasmid DNA is usually delivered using biological (viruses), chemical (lipid-based or chemical polymers), or physical (electroporation, magnetofection, injection) methods. However, many cell types, for example cells such as primary cells and stem cells, remain 'hard to transfect'.

A wide range of methods can be used to chemically 'permeabilize' cells and tissues. Many of these methods do not attempt 'reversible permeabilization' and do not focus on delivery into a living cell. Instead, the methods aim at 'irreversible permeabilization' to deliver a 'label' that will attach to a molecule or structure within a cell or tissue for purposes such as visualization or quantification (for example, immunofluorescence). In these situations, the cells and tissues are non-viable following permeabilization. Chemicals typically used in these methods include alcohols (which dissolve lipids in a plasma membrane), detergents (which create pores in a plasma membrane) and enzymes (which digest proteins and create pores in a plasma membrane).

Generally provided herein are methods, systems, and apparatuses related to delivery across cell membranes, and especially delivery across cell membranes such that the cells remain viable. Payloads can be delivered across membranes and into cells through a variety of means, such as by using a microfluidic chip to mix cells and a solution including any payload. The process, device and system provided herein have a variety of benefits over various other processes currently used. For example and provided herein as non-limiting examples, the process discussed herein can achieve homogeneous delivery of a variety of payloads within a population of cells. Delivery can be accomplished to cells in suspension, as well. The process can allow user control of a variety of delivery process parameters, such as temperature (for example with a controlled hotplate substrate), humidity, a number of cells to which a payload can be delivered, permitting microscopic visualization and machine vision cell counting and/or flow rate control, and/or introduction of a stop solution via a downstream mixing element. Generally the process herein converts a process that may be fast and/or dynamic, resulting in a process that is difficult to control, into a process that may be more controllable. For instance, a user may gain control over osmolarity and diffusion rates. The process provided herein is also a closed process that provides better and consistent transfection efficiency, and viability and cell functionality. The process may thus generally address reversible membrane permeabilization through fluidic contacting and/or mixing and provides control over delivery across cell membranes.

In one embodiment, compounds or mixtures of compounds (i.e. compositions) can be delivered into cytoplasm of eukaryotic cells by contacting the cells with a solution containing one or more compounds and/or compositions to be delivered (e.g., a payload) and an agent that reversibly permeates and/or reversibly dissolves a cell membrane. In some embodiments, the solution can be mixed with the cells in channels of a microfluidic chip, for example through multiple passive or active mixing elements. Additionally, the cells can be mixed with the compound-containing solution at a controlled flow rate and over a controlled time in a temperature and humidity controlled environment. Exemplary agents that permeate or dissolve a eukaryotic cell membrane include alcohols, such as ethanol, and detergents, such as Triton X-100. Other exemplary detergents, e.g., surfactants, can include polysorbate 20 (e.g., Tween 20), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), sodium dodecyl sulfate (SDS), and octyl glucoside.

Figure 2:
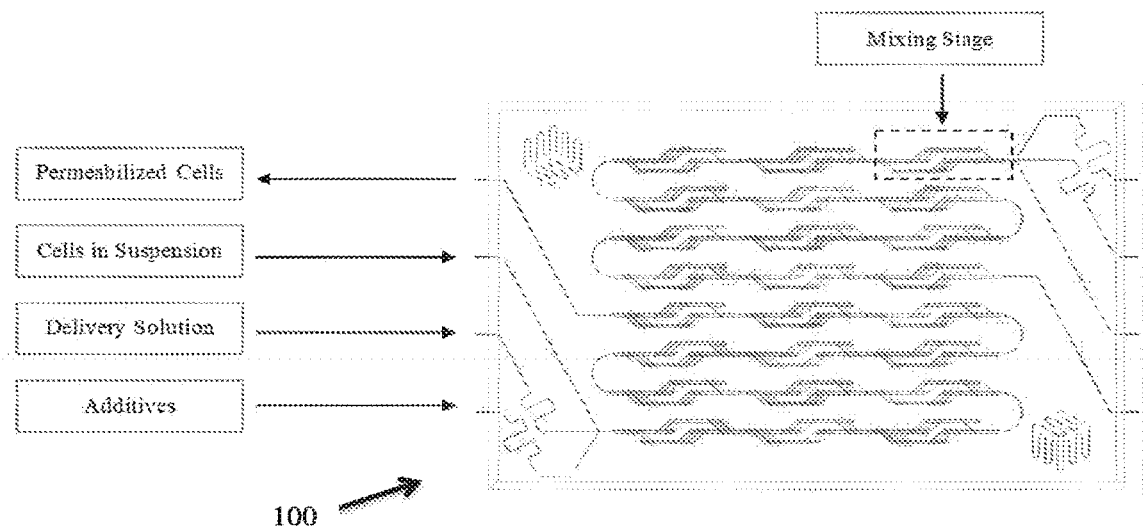
FIG. 2 is a schematic view of the microfluidic mixing chip of FIG. 1.

FIGS. 1-6 illustrate one embodiment of a system and a method of delivery across a cell membrane. FIG. 1 illustrates a microfluidic mixing chip 100 that can be used herein. The chip can take a variety of forms. For example, the microfluidic mixing chip shown in FIG. 1 is manufactured by Dolomite Microfluidics, UK. However a variety of different chips can be used. The embodiment shown herein permits laminar flow mixing at low throughput volumes and also turbulent mixing at higher throughput volumes, but various other approaches can be taken. The chip 100 includes multiple mixing stages, illustrated further in FIG. 4. As illustrated in FIG. 2, cells are first introduced into the mixing chip 100 in suspension at a controlled flow pace. Illustrated herein are T cells, but a variety of cells can be used. Approximately simultaneously with the cells, a delivery solution and additives are introduced into the mixing chip 100. The delivery solution includes any of a number of known permeabilizing agents, such as those discussed above that reversibly permeates and/or reversibly dissolves a cell membrane, and the delivery solution contains a delivery payload, such as messenger ribonucleic acid (mRNA), to be delivered across membranes of the cells introduced to the chip 100. One or more additives can optionally be used in the process, and the additives can take a variety of forms. The chip 100 illustrated in FIG. 1 has two different mixing circuits, and each mixing circuit has 12 mixing stages or channels and can mix up to 3 streams of fluids. However, a variety of mixing circuits, mixing stages, and/or streams can be used. Mixing of the cells thus can include a ratio of volume of fluid to cell volume. Alternatively, mixing can include a ratio of volume of fluid to exposed cell area, for example area of cell membrane that is exposed when the cells exist in suspension in channels of a mixing chip such as chip 100 and/or arrangement of fluidic tubes that effect mixing.

Over the course of 12 mixing stages, the cells are permeabilized by controlled contacting with the delivery solution as the cells and the delivery solution are mixed in the mixing chip 100. The cells and the delivery solution experience laminar flows in the mixing chip 100, but the laminar flows within the mixing chip 100 in this illustrated embodiment are broken up by internal fluidic structures within the chip 100 exposing surfaces of the cells to permeabilization through contrast contacting. There are a variety of ways to permeate the membrane of a population of cells, such as controlled volumetric contacting of cells in suspension with payload delivery solution over a time interval. A user can control many aspects of the mixing process. For example, the user can control speed, temperature, humidity in the process in the visualization of this process.

Figure 3:
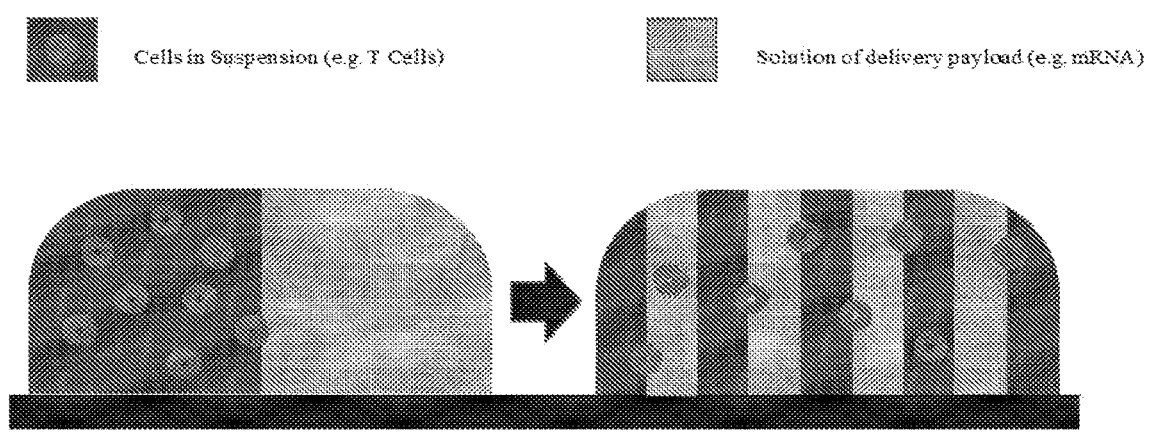
FIG. 3 is a diagram illustrating mixing of cells in suspension and of a delivery solution in a microfluidic mixing chip such as that shown in FIG. 1.
Figure 4:
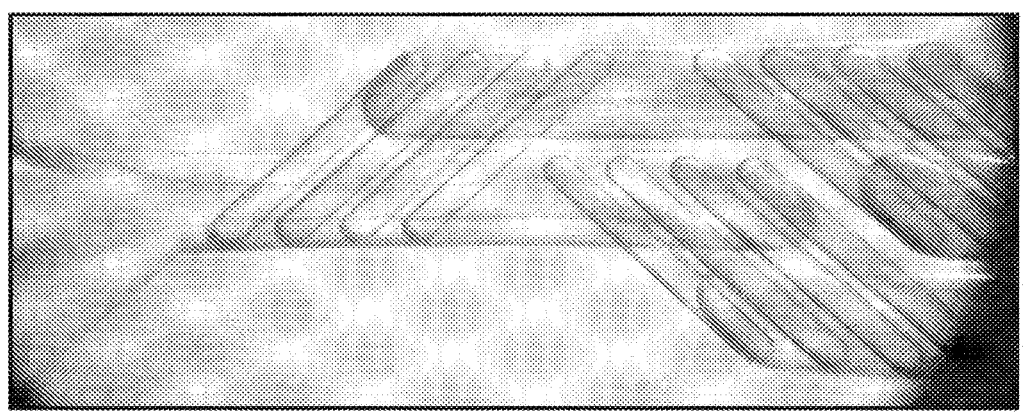
FIG. 4 is a top down view of a mixing stage in a microfluidic mix such as a shown in FIG. 1.

As illustrated in FIG. 3, the embodiment shown herein creates multiple laminar flows, and the cells in suspension contact the delivery solution containing the delivery payload. For example, FIG. 4 illustrates mixing activity in one of the multiple mixing stages of the chip 100, showing laminar flows with contacting and mixing of fluid streams (provided in FIG. 4 using alkali, acid, and potassium permanganate indicators). As the cells and the delivery solution mix through the chip 100, permeabilized cells are output by the chip 100 after a first mixing cascade. The permeabilized cells, representing an output of the chip 100 after the first mixing cascade, can be fed into an input on the chip 100 of the second mixing cascade, as illustrated in FIG. 5.

Figure 5:
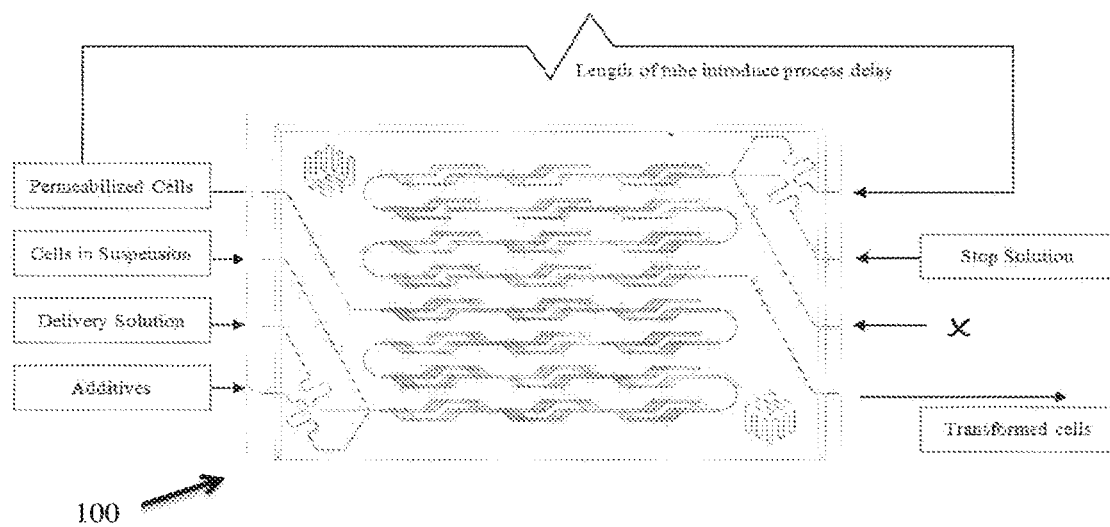
FIG. 5 is a schematic view of the microfluidic mixing chip of FIG. 1.
Figure 6:
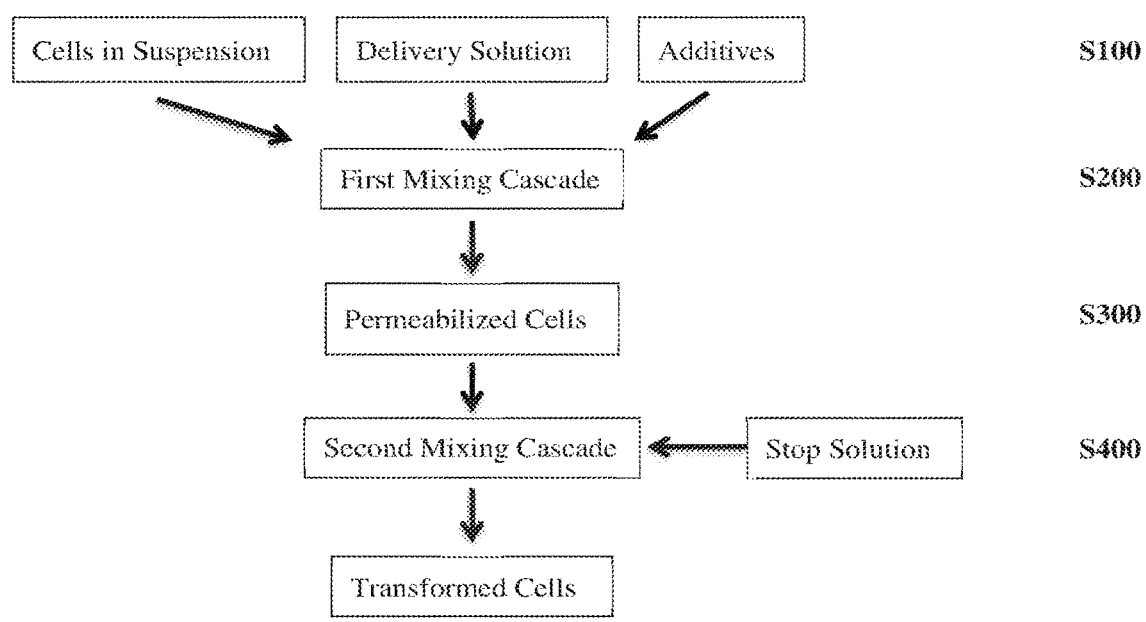
FIG. 6 is a diagram of a process of using the microfluidic mixing chip of FIG. 1.

Also illustrated in FIG. 5 is introduction of a stop solution. A subsequent introduction of a second solution, the stop solution, to stop permeabilization provides greater control to a user during the mixing process. A user can further introduce a controllable delay before the stop solution is mixed with the permeabilized cells. For example, a length of a feedback tube used to introduce the permeabilized cells to the second mixing cascade can be varied. During the second mixing cascade shown in FIG. 5, the permeabilized cells are mixed with the stop solution to stop permeabilization of the cells. A subsequent output of the second mixing cascade, and the overall process, is cells that have been transformed and/or transfected with the delivery payload of the delivery solution. The transformed cells resulting from the process provided herein have characteristics that are enhanced over cells resulting from other processes. FIG. 6 diagrams delivery of a payload to cells through the overall process described herein.

In operation, referring to FIG. 6, the method of delivering payloads across cell membranes in a continuous flow platform may include introducing a population of cells and a delivery solution into a microfluidic mixing chip (step S100), causing the population of cells and the delivery solution to mix in the first mixing cascade (step S200), allowing the interaction between the population of cells and the delivery solution to transfer a delivery payload from the delivery solution to the population of cells across membranes of the population of cells (step S300), and further introducing a stop solution to the population of cells and the delivery solution subsequent to transfer of the payload across the membranes of the population of cells such that the stop solution may prevent any additional transfers across the membranes of the population of cells (step S400).

For FIGS. 1-6, diameters of the cells are smaller than a width of the mixing channels of the chip 100. A narrowest channel of the chip 100 is approximately 5 to 10 times larger than the diameters of the T cells in the illustrated embodiment. However, a variety of sizes and ratios between channel size and cell diameter can be used, especially to be configured to allow an optimized ratio between a cell size and/or diameter and a channel size and/or width such that the ratio optimizes mixing and/or controlled contact. In various embodiments, a smallest dimension of a channel in a mixing chip will be greater than a cell size and/or diameter. A clinically relevant therapeutic dose of cells may number $10 \times 10^{10}$ or more, and the number of mixing cascades on one or more mixing chip and/or a process flow rate may be optimized for this therapeutic dose, especially such that a clinically relevant sample of cells may be transformed into an acceptable process time.

Figure 7:
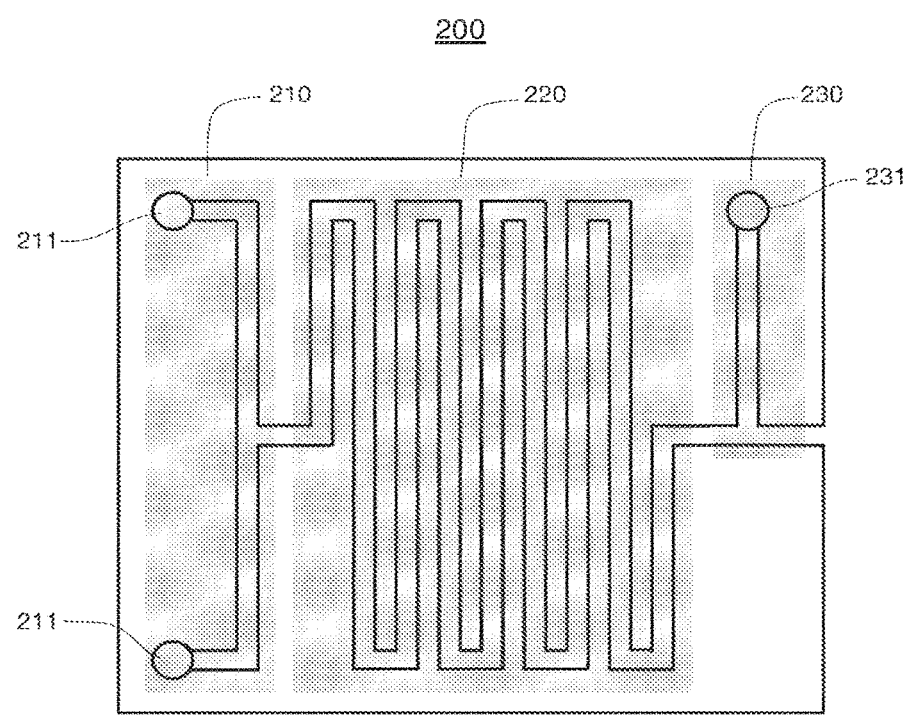
FIG. 7 is a schematic diagram of a microfluidic device according to an exemplary embodiment.
Figure 8:
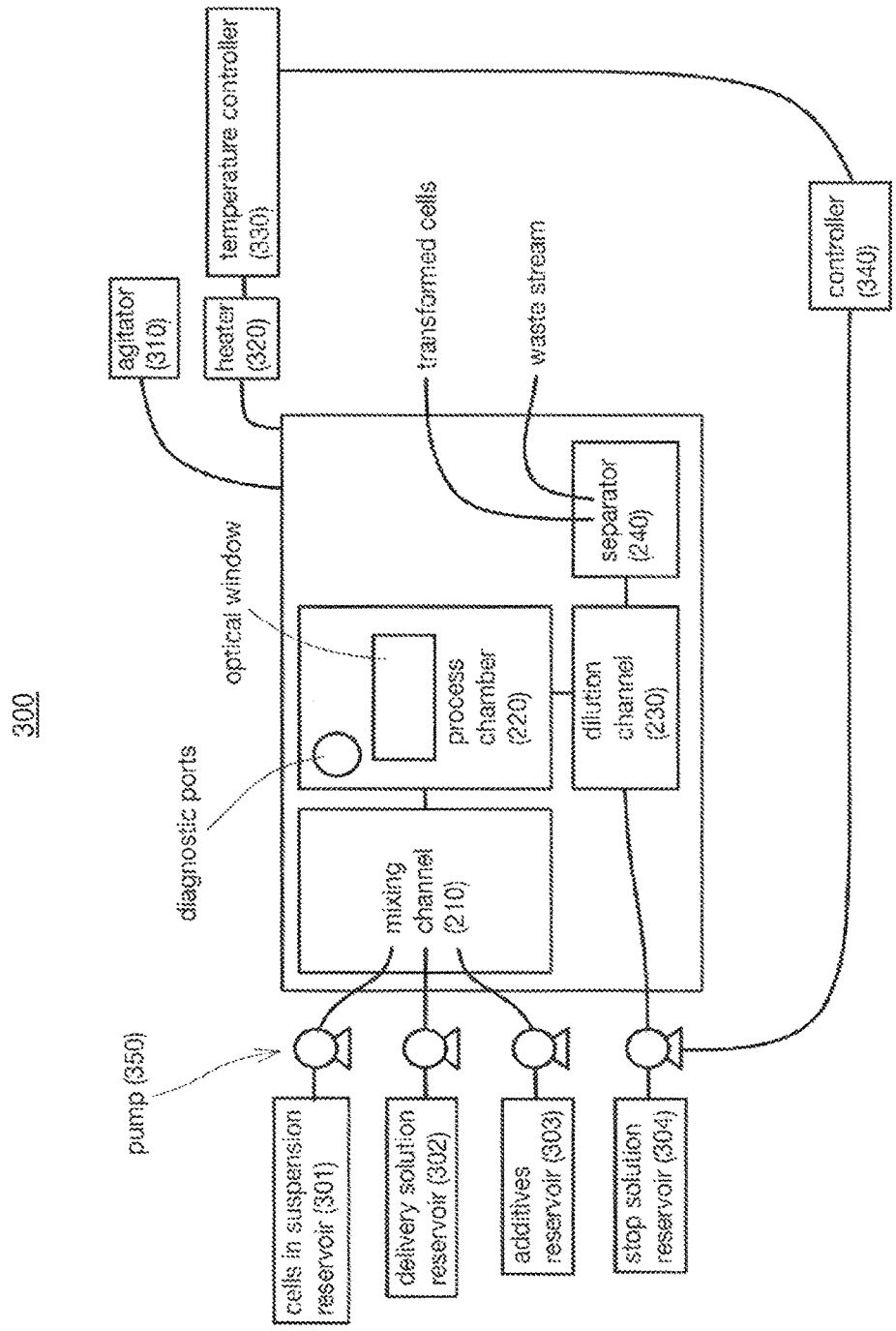
FIG. 8 is a schematic diagram of a system for delivery of payloads across cell membranes including the microfluidic device according to an exemplary embodiment.

FIGS. 7 and 8 illustrate other embodiments of the microfluidic device and system for delivery of payloads across cell membranes. Referring to FIGS. 7 and 8, the microfluidic device 200 can be made on a substrate that includes three microchannel parts: a mixing channel 210, a process chamber 220, and a dilution channel 230. The mixing channel 210 can receive reactant streams, e.g., a suspension including a population of cells, a delivery solution including a delivery payload, and various additives, through a plurality of inlets 211. The reactant streams supplied through the inlets 201 can be combined and mixed in the mixing channel 210. To enhance mixing, the mixing channel 210 can include microchannels that are arranged in, e.g., a herringbone pattern, an interdigitated pattern, and/or a double T pattern.

Figure 9:
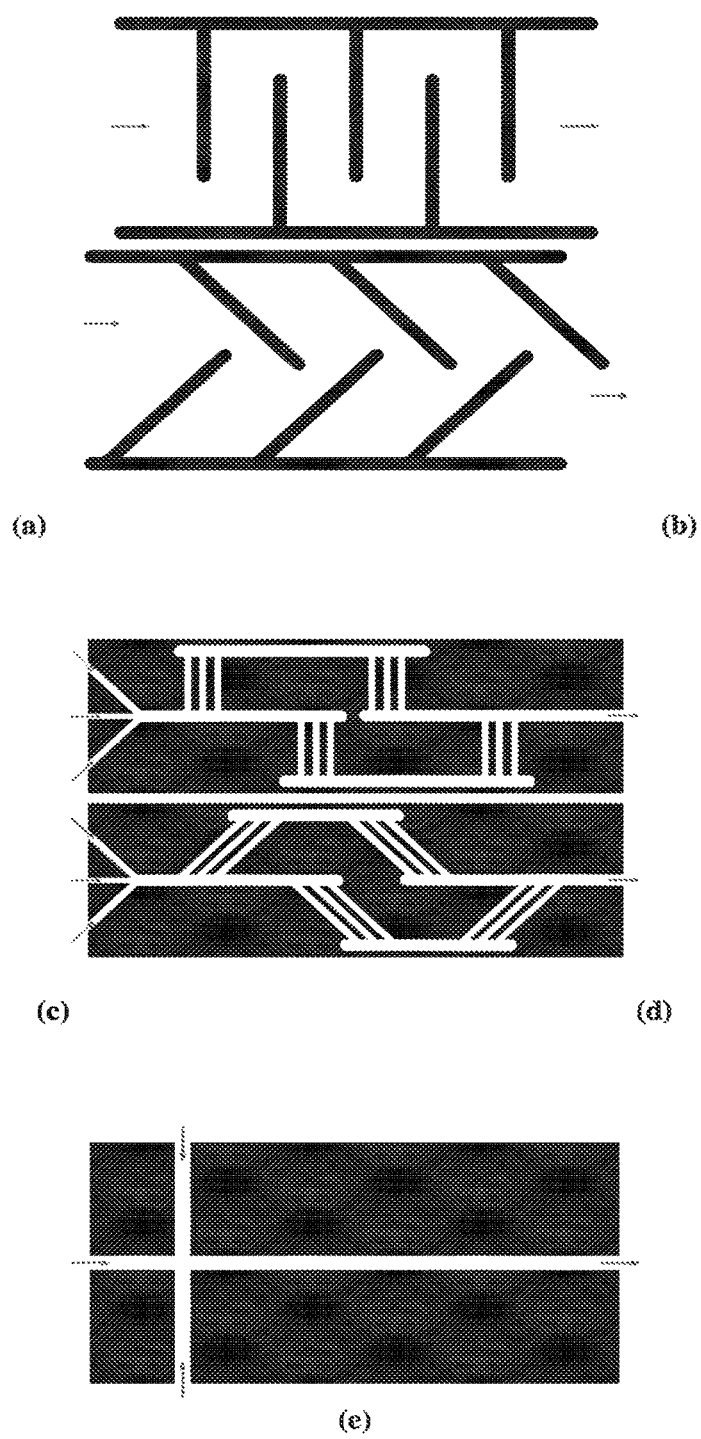
FIG. 9 illustrates exemplary geometries for a mixing channel of the microfluidic device: (a) serpentine passage, (b) herringbone-shaped passage, (c) interdigitated split-recombination configuration, (d) herringbone-shaped split-recombination configuration, and (e) double-T configuration.

FIG. 9 illustrates non-limiting examples of the microchannel geometries of the mixing channel 210. FIG. 9(a) shows an example of a serpentine flow path around path-defining walls that are formed in an interdigitated pattern. In this configuration, numerous recirculation zones can be created around the tip of the walls and/or at corners, and also a secondary flow can be developed as the flow turns and bends. The recirculation and the secondary flow may enhance mixing of the cell suspension and the delivery solution.

FIG. 9(b) shows an example of the walls of the mixing channel that are formed in a herringbone pattern, which can provide similar effects as the interdigitated pattern. FIG. 9(c) illustrates an exemplary implementation of the mixing channel formed in an interdigitated split-and-recombination configuration. Three streams that come in through each of the inlets can be combined to a middle channel and subsequently experience a split into an upper channel and a lower channel through a plurality of proximal sub-channels and then be recombined to the middle channel through a plurality of distal sub-channels. This arrangement can be repeated multiple times to achieve a mixing to a desired level. Through multiple split and recombination processes, even a laminar flow can be effectively mixed. An illustration of the split-and-recombination mixing is also shown in FIGS. 3 and 4.

FIG. 9(d) illustrates an exemplary implementation of the mixing channel formed in a herringbone-shaped split-and-recombination configuration, of which operating principle is similar to the interdigitated split-and-recombination configuration of FIG. 9(c). FIG. 9(e) shows an example of a double T (e.g., a cross) type mixing channel. The double T type mixing channel may be used as stand-alone mixing channel 210 or in combination with other mixing channel configurations by disposing it at upstream of other configurations described above. The mixing channel patterns and configurations disclosed herein and in FIG. 9 are merely for illustrative purposes. The channel arrangement patterns are not limited thereto and can include various other patterns and structures. The mixing channel 210 can include a channel width between 0.01 µm and 100 µm, 100 µm and 1 mm, or greater than or equal to 1 mm. The channels can have a uniform width throughout, or alternatively have a varying width.

After being mixed in the mixing channel 210, the reactant streams can be supplied to the process chamber 220. In the process chamber 220, the mixture of the suspension and the delivery solution can be retained for a predetermined residence time and be permeabilized therein. The residence time within the process chamber 220 may be in a range between 0.01 and 60 minutes, for example from 0.01 to 0.1 minutes, 0.1 to 1 minutes, from 1 to 5 minutes, from 5 to 10 minutes, from 10 to 30 minutes, or greater than or equal to 30 minutes.

Figure 10:
FIG. 10 illustrates exemplary geometries for a process chamber of the microfluidic device: (a) straight channel shape, (b) serpentine channel shape, and (c) circular channel shape.
Figure 10:
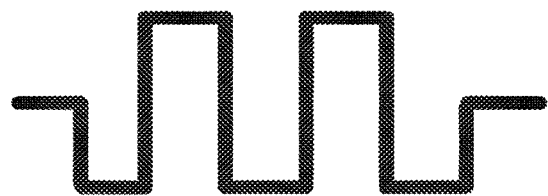
Figure 10:
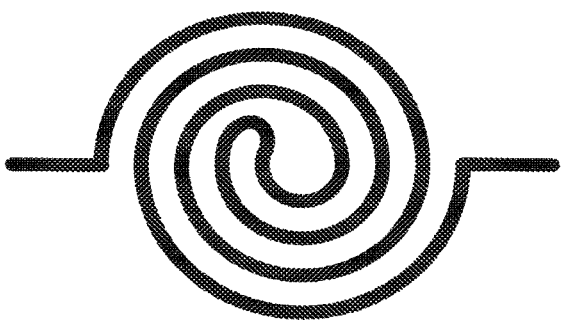

The process chamber 220 can be implemented in various geometries. For example, for a continuous flow process, the process chamber 220 can be made as a microchannel in a straight channel shape, a serpentine channel shape, and/or a circular channel shape. FIG. 10 illustrates non-limiting examples of the geometries of the process chamber 220. FIG. 10(a) shows an exemplary implementation of the process chamber 220 arranged in a straight channel shape. The straight channel shape is simple to fabricate and easy to characterize the flow residence time. FIG. 10(b) shows an exemplary implementation of the process chamber 220 arranged in a serpentine channel shape. With the serpentine channel shape, a long channel can be included in a relatively small area, and thereby increasing the area utilization of the substrate.

FIG. 10(c) shows an exemplary implementation of the process chamber 220 arranged in a circular (or spiral) channel shape. Similar to the serpentine channel shape, the circular channel shape can include a long channel length within a small area. The geometry of the process chamber 220 is not limited thereto, however. The cross-sectional area, cross-sectional geometry, and length of the microchannel of the process chamber 220 can be determined based on the overall flow rate and desired residence time of the mixture of the suspension and the delivery solution. The process chamber 220 can include a channel width between 0.01 µm and 100 µm, 100 µm and 1 mm, or greater than or equal to 1 mm. The channels can have a uniform width throughout, or alternatively have a varying width.

Figure 14:
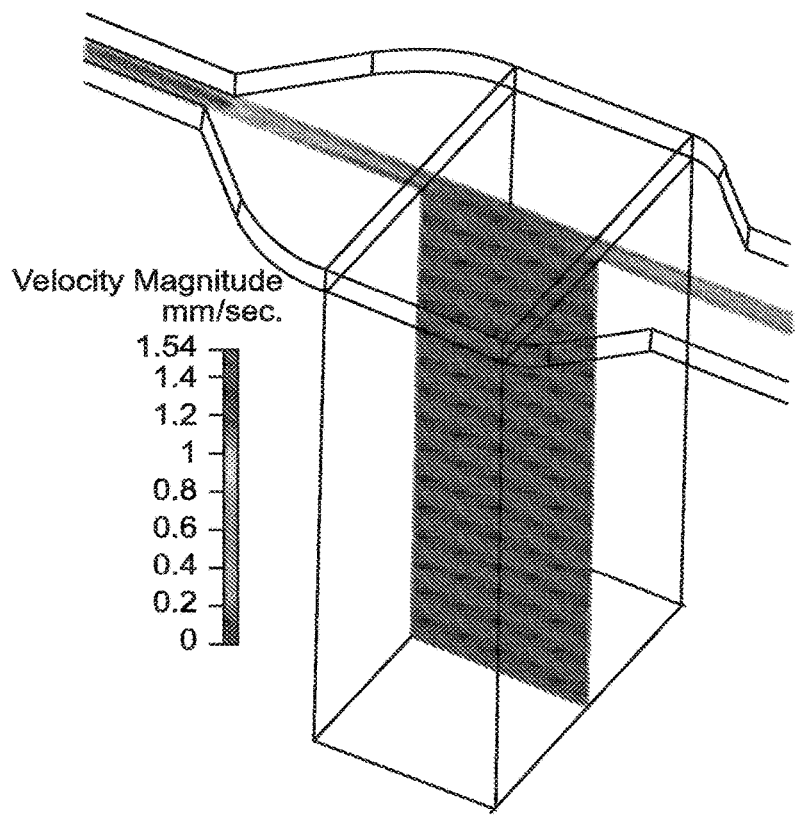
FIG. 14 illustrates exemplary implementation of payload delivery across cell membranes using a trench-type batch process chamber (a) simulation of cell capture based on sedimentation of cells to the bottom of the trench structure, and (b) operating principle of the trench-type process chamber.
Figure 14:
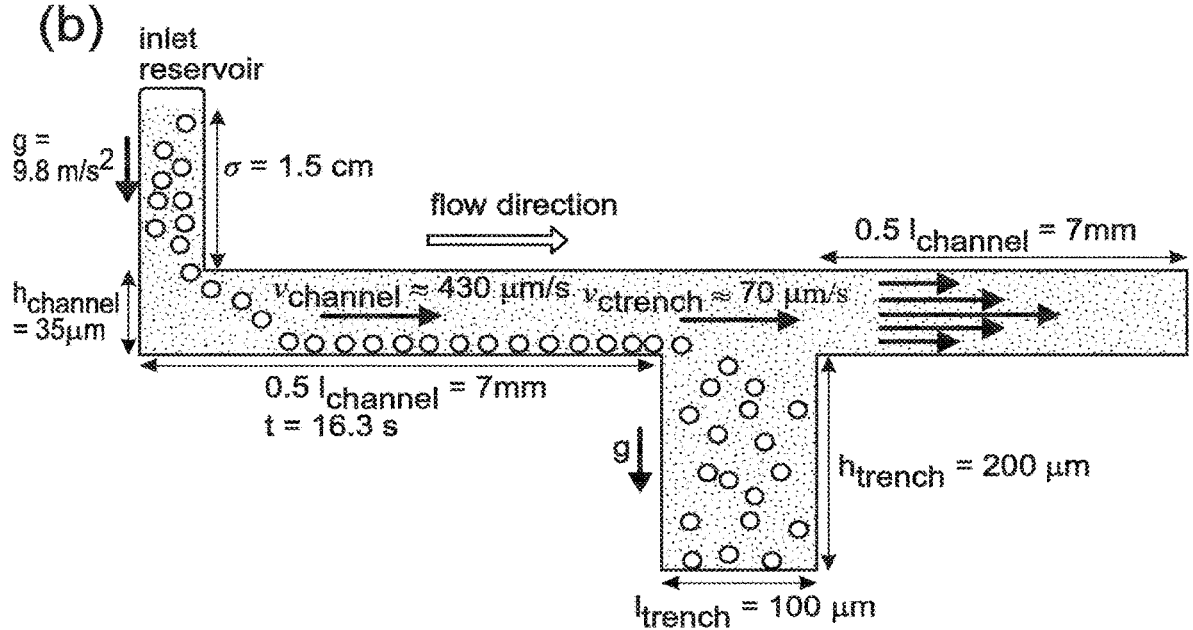

For a semi-continuous (e.g., continual batch) process, the process chamber 220 can be made as a plenum having a particular volume. An example of the process chamber 220 implemented as a plenum is shown in FIG. 14. A trench-type plenum is shown in FIG. 14, but the process chamber 220 is not limited to the trench-type plenum. It can be formed in various other geometries, including, but not limited to, a cube, a sphere, and a cylinder.

In embodiments, the plenum-type process chamber can also be implemented in a system using a continuous flow process. In these embodiments, small inlet/outlet and relatively large plenum volume might make it difficult to characterize the residence time due to formation of recirculation zones. If uncharacterized residence time is undesirable, a continuously stirred reactor may be used, in which a stirrer is included in the process chamber 220. The stirrer can be directly connected to an electrical motor or can be driven magnetically. If so desired, a packed-bed reactor can also be used. In general, the packed-bed reactor can straighten out the fluid flow, and make the flow resemble a plug flow, for which the flow residence time is easy to characterize.

The process chamber 220 can further include at least one diagnostic ports such as a temperature port, a pressure port, and a sample extraction port. The temperature port can accommodate a temperature probe including, but not limited to, a thermocouple, a resistance temperature detector (RTD), a thermistor, a semiconductor-based sensor and/or a non-contact type infrared sensor. The temperature measurement can be used to monitor the process temperature, and further to be fed to a temperature controller for a feedback temperature control, which will be described later.

The pressure port can be connected to a pressure sensor including, but not limited to, a strain-gauge, a piezoelectric sensor, an electromagnetic sensor, piezoelectric sensor, and/or an optical sensor. The pressure measurement can be used to monitor the process pressure, and further to be fed to a controller for a feedback control of process parameters such as flow rates. The process pressure can be controlled between 0.9 atm to 1 atm, 1 atm to 1.5 atm, or greater than or equal to 1.5 atm for efficient translocation of the payloads across the cell membranes.

A sample can be extracted through the sample extraction port for in-line and/or off-line analysis. The extracted sample can be analyzed to determine the process parameters. The extracted sample can inform acceptance or rejection of products of the process, can inform the halting of the process or modification of the process parameters. In a cell therapy manufacturing example, the cells engineered via the process can be sample tested for viability, functionality, efficiency of expression, proliferative capacity, presence or absence of a gene or toxicity.

Furthermore, to enhance diagnostic capabilities and to provide an analytical feedback, the process chamber 220 can also include an optical window made of an optically transparent material. Optical analysis methods include, but not limited to, optical still/movie imaging, optical/electron microscopy, spectroscopic techniques such as Raman spectroscopy, absorption spectroscopy, and emission spectroscopy. The diagnostic measurements can be used in real-time for a feedback control of the process or be used off-line for post-analysis. The optical window may be made of a yellow-tinted glass to prevent ultraviolet ray from causing photoactivated reactions. As an exemplary implementation, the optical window can be made by bonding an optically transparent substrate on top of the substrate that includes the process chamber 220. Alternatively, the substrate that includes the process chamber 220 can include etch-through features that define the process chamber 220, and be sandwiched between two optically transparent substrates on top and bottom thereof, respectively. The bonding of the optically transparent substrate to the device substrate may be accomplished by anodic bonding, fusion bonding, and/or using an adhesive. In other implementations, the optical window may be included in at least one of the mixing channel 210, the dilution channel 230, or a separator 240, which is further described below.

Examples of the analyses that can be performed through the optical window include the following. Optical still images can be obtained to visualize the process. An optical and/or a microscopic video can be obtained to visualize the fluid/cell flows in the process chamber. The visualization can perform cell counting, flow rate monitoring, or the like. Optical analysis can further include more sophisticated methods such as spectroscopic techniques. The optical analysis results can be further used to control the process through a controller 340. In operation, the controller 340 may adjust the flow rates by controlling a pump 350.

After being permeabilized in the process chamber 220, the mixture of the suspension and the delivery solution may flow into a dilution channel 230. In the dilution channel 230, the processed fluid out of the process chamber 220 can be mixed with a stop solution that is supplied through an inlet 231. The dilution channel 230 can be configured as a simple fluidic channel, or include more structures such as the various patterns illustrated in FIG. 9 for the mixing channel 210 to enhance mixing between the processed fluid and the stop solution. The stop solution can decrease or stop the permeabilization of the cell membrane and can therefore reduce or prevent additional payload delivery across the membranes of the population of cells, providing a better control of the process. In examples, the stop solution can include phosphate buffered saline (PBS). The concentration of PBS can be about 0.5×PBS.

In addition, a separator 240 can be further included in the device and connected at the end of the dilution channel 230 to isolate transformed cells from a waste stream. The separator may be implemented in a form of a dead-end filter or across-flow filter. The implementation of the separator is not limited thereto, however, and can include various other implementations that separate the processed cells from the waste stream.

The substrate of the microfluidic device 200 can be made of a material including silicon, silicon oxide, silicon carbide, silicon nitride, silicate glass, borosilicate glass, quartz, sapphire, or polymers such as polydimethylsiloxane (PDMS), polyethylene, polypropylene, polyurethane, polytetrafluoroethylene (PTFE), or polyether ether ketone (PEEK). The substrate may be coated in indium in oxide (ITO) or may be made from stainless steel as well. The stainless steel can include chromium-manganese-nickel alloys, chromium-nickel alloys, or the like. The stainless steel can include, for example, 304 grade stainless steel or 316 grade stainless steel. The substrate can be fabricated by machining techniques and/or various microfabrication techniques including, but not limited to, wet and dry etching, ultrasonic machining, and/or laser machining. The microchannel can have widths that are suitable for the application. Particularly, the widths of the microchannels can be in ranges of 0.01 μm and 100 μm, 100 μm and 1 mm, or larger.

A schematic diagram of a system 300 for payload delivery across cell membranes 300 including the microfluidic device 200 is shown in FIG. 8. The system 300 can further include various components to support the operation of the microfluidic device 200. In embodiments, the system 300 can be implemented as a closed system, in which all fluidic channels and connections are sealed such that the cells and the reagents are not exposed to external (e.g., ambient) elements during the payload delivery process. The closed system can enable a sterile transfection, which makes it suitable for therapeutic uses.

The system 300 can include a cell suspension reservoir 301. In some embodiments, the cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. In embodiments, the population of cells can include non-adherent cells, e.g., the % non-adherent cells in the population can be at least 50%, 60%, 75%, 80%, 90%, 95%, 98%, 99% or 100% non-adherent cells. Non-adherent cells may be primary cells as well as immortalized cells (e.g., cells of a cell line). Exemplary non-adherent/suspension cells include primary hematopoietic stem cell (HSC), T cells (e.g., (cluster of differentiation 3) CD3+ cells, (cluster of differentiation 4) CD4+ cells, (cluster of differentiation 8) CD8+ cells), natural killer (NK) cells, cytokine-induced killer (CIK) cells, human cord blood CD34+ cells, B cells, or cell lines such as Jurkat T cell line. Non limiting examples of T cells may include CD8+ or CD4+ T cells. In some aspects, the CD8+ subpopulation of the CD3$^+$ T cells can be used. CD8$^+$ T cells may be purified from the PBMC population by positive isolation using anti-CD8 beads.

In examples, cells can be cultured in standard cell culture media, e.g., complete RPMI (Roswell Park Memorial Institute medium) using RPMI basal medium, heat-inactivated fetal bovine serum (FBS), e.g., about 10% by volume, penicillin-streptomycin, and L-glutamine. In some examples, the standard culture media can be supplemented with cytokines, e.g., Interleukin-2 (IL-2) (200 U/ml). In embodiments, the cytokines can be at a concentration from about 10 U/ml to about 500 U/ml. In other examples, the cytokines can be at a concentration of about 50 U/ml, about 100 U/ml, about 200 U/ml, about 300 U/ml, about 400 U/ml, or about 500 U/ml. The cytokine concentration can be about 200 U/ml.

Further, the system 300 can include a delivery solution reservoir 302. The delivery solution (e.g., including a cargo molecule) includes an alcohol such as ethanol in an amount between 1-30% alcohol. The delivery solution can include an isotonic aqueous solution, the aqueous solution including the payload and an alcohol at greater than 5% concentration by volume. In embodiments, the alcohol concentration can be in a range between 2 to 5% by volume, for example, 2%, 3%, 4% or 5%. The alcohol can include ethanol. The aqueous solution can include greater than 10% ethanol. The aqueous solution can include between 20-30% ethanol. The aqueous solution can include 27% ethanol. The aqueous solution can include between 12.5-500 mM KCl (potassium chloride). The aqueous solution can include between 106 mM KCl. In some embodiments, the aqueous solution can include an ethanol concentration of 5 to 30%. The aqueous solution can include one or more of 75 to 98% H$_2$O, 2 to 45% ethanol, 6 to 91 mM sucrose, 2 to 500 mM KCl, 2 to 35 mM ammonium acetate, and 1 to 14 mM (4-(2-hydroxyethyl)-1-piperazineethanesulfonic acid) (HEPES). For example, the delivery solution can contain 10$^6$ mM KCl and 27% ethanol. In other embodiments, the payload delivery solution can include 25% of the alcohol by volume. Alternatively, the payload can include 2-8% of the alcohol by volume, or 2% of the alcohol. The alcohol may include ethanol and the payload comprises 5, 10, 20, 25, 30, and up to 40% or 50% of ethanol by volume, e.g., 27%. Example methods may include methanol as the alcohol, and the payload may include 5, 10, 20, 25, 30, or 40% of the methanol by volume. The payload may include 2-45% of methanol by volume, 20-30% or 25% methanol by volume. The payload can include 20-30% of methanol by volume. Further alternatively, the alcohol may include butanol and the payload may include 2, 4, or 8% of the butanol by volume.

The system 300 can include a stop solution reservoir 304. In examples, the stop solution can include phosphate buffered saline (PBS). The concentration of PBS can be about 0.5×PBS. In some implementations, the S-buffer can be formulated by a GMP (Good Manufacturing Provider) provider and can be provided in a foil-top 10 mL vial. Separate DMF (dimethylformamide) can be put on file for S Buffer.

In addition, the system 300 can include an agitator 310 that applies agitation by means of a low frequency pressure pulse, an ultrasonic vibrator, a mechanical vibrator, or the like. The vibration or percussive force can be applied selectively to at least one of the mixing channel 210, the process chamber 220, the dilution channel 230 or the separator 240 and/or applied to the entire device 200. Applying vibration can increase chances for the cells and the payload to collide with each other and enable consistent and uniform contact between the cells and the payload, resulting in better consistency and control. Agitation may maintain cargo at the cell membrane and assist the diffusion process. Agitation may also promote uptake of payload by the cell by mechanically stimulating the cell membrane.

The system 300 can also include a heater 320 and a temperature controller 330 to maintain or vary the temperature of the entire device or particular parts of the device. The heater 320 and the temperature controller 330 can include a single heating zone or a plurality of heating zones. The temperature controller 330 may take an input from the temperature probe that is disposed within the process chamber 220 and generate a feedback control signal to operate the heater 320. The heater 320 can be implemented as a resistive heater and/or an infrared heater. Controlling the process temperature can enhance consistency of the process since the reactivity of the reagents, biological responses of the cells and cell membranes, and fluid flows are affected by the process temperature. Introducing a thermal gradient using the heater between zones on the substrate can facilitate cold-shock, which can promote intercellular delivery.

The system 300 may include an additive reservoir 303. In the additive reservoir 303, one or more additives can be stored to be used in the process, and the additives can take a variety of forms. For example, the additives can stabilize a protein-based payload and/or can enhance the solubility of payload.

At least one pump 350 may be further be included in the system 300 to continuously supply the fluids in the reservoirs to the respective inlets. In embodiments, each reservoir can include a pump. Moreover, the system 300 can include a controller 340. The controller 340 may log and/or process data streams that are input from the temperature sensor, the pressure sensor, and various other sensors. The controller 340 may also generate control signals for the temperature controller 330 and/or pump 350 to adjust the process temperature and/or the flow rates, respectively. The controller 340 may further include a computer or a similar user interface device to interact with an operator of the system 300.

Some implementations of the current subject matter provides a cell engineering platform that can scale a technique of delivery of payloads into cells. The platform may achieve delivery to a large number of cells quickly. The platform can be made as a closed system. In some implementations, the current subject matter can enable sterile transfection, deliver mRNA and RNP to primary T cells, and other cells. Moreover, the platform can be easy to use and can enable repeatable and consistent delivery.

In some implementations, the current subject matter relates to delivery technology that facilitates delivery of a broad range of payloads to cells. Compared to batch processes, some implementations of the continuous flow platform to deliver payloads across cell membranes can enable a steady-state process in which the concentrations of the cells, payloads and permeabilization agents can be maintained in a steady-state over time. Accordingly, some aspects of the continuous flow platform can provide better consistency throughout the operation, can yield a high throughput to cover the therapeutic capacity range, and can possess a better scale-up potential.

Example 1

In an example of the process provided herein, an automated syringe pump was loaded with 2×1 mL Hamilton syringes and set to a flow rate of 500 µL per minute. Syringe A contained 500 µL Avectas delivery solution containing 50 µg propidium iodide (PI; 150 µM). Syringe B contained 500 µL of a $2 \times 10^7$ cells per mL solution of Jurkat cells in media. The syringes were connected to a Dolomite mixing chip such that Syringe A was connected to Inlet 2 and Syringe B was connected to Inlet 3. Inlet 1 was blocked off. The chip was primed with both cells and delivery solution containing PI. Once a pump was activated to run at 500 µL per minute, samples were collected at 30 s intervals (each sample contained 50 µL and $5 \times 10^5$ cells). The first sample was discarded (priming mixture) and the remaining 5 samples were incubated at RT for 1, 1.5, 2, 2.5 and 3 minutes respectively. A stop solution (0.5×PBS; 150 µL) was added for 30 s and the complete Jurkat media then added (300 µL). The cells were allowed to rest for 5 min before being prepared for flow cytometry. Cells were centrifuged at 500×g for 5 minutes, the supernatant discarded, and the cells resuspended in 150 µL PBS. The cells were analyzed by flow cytometry for presence of intracellular PI. Controlled mixing via the Dolomite mixing chip induced PI uptake in each samples with a maximum uptake of 11.8% (2 minute) compared with control cells.

The devices disclosed herein can also be designed to be disposed of after a single use, or they can be designed to be used multiple times. Components of the current subject matter described herein can be processed before use. First, a new or used instrument can be obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility. If the device is sterilized, this can be done in a variety of other ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114, 345 filed Feb. 8, 2008 and entitled "System And Method Of Sterilizing An Implantable Medical Device." It is preferred that device, if implanted, is hermetically sealed. This can be done by any number of ways known to those skilled in the art.

Example 2

Figure 11:
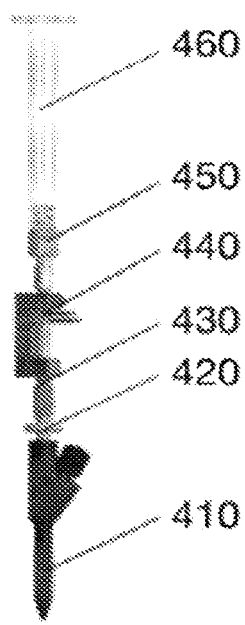
FIG. 11 shows an exemplary implementation of payload delivery across cell membranes using a spray method including a syringe.
Figure 12:
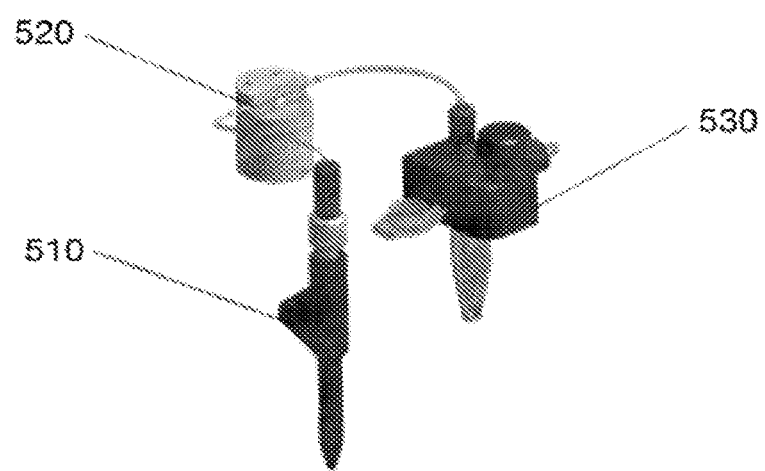
FIG. 12 shows an exemplary implementation of payload delivery across cell membranes using a spray method including a pump.

In some embodiments, the payload delivery across the cell membranes can be implemented with a spray method. FIGS. 11 and 12 illustrate two exemplary implementations for the spray method that were tested. In the exemplary embodiments of the spray methods, a suspension containing cells is mixed with a delivery solution containing a payload, and the mixture is injected through a nebulizer through which the mixture breaks up into fine droplets. The nebulized droplets are collected on a plate having a plurality of well structures to contain liquid. After a certain residence time (e.g., incubation time), a stop solution is applied, and subsequently the processed specimens are analyzed.

Unlike a batch process using a monolayer approach, the spray method may not require formation of a monolayer to deliver a payload (e.g., nucleic acids) to cells (e.g., human T cells). In addition, the spray method may not require a use of a filter plate, and thus the cells can be retrieved easier due to lack of a filter mesh. Moreover, the spray method can be adapted to include a continuous flow throughput.

Figure 13:
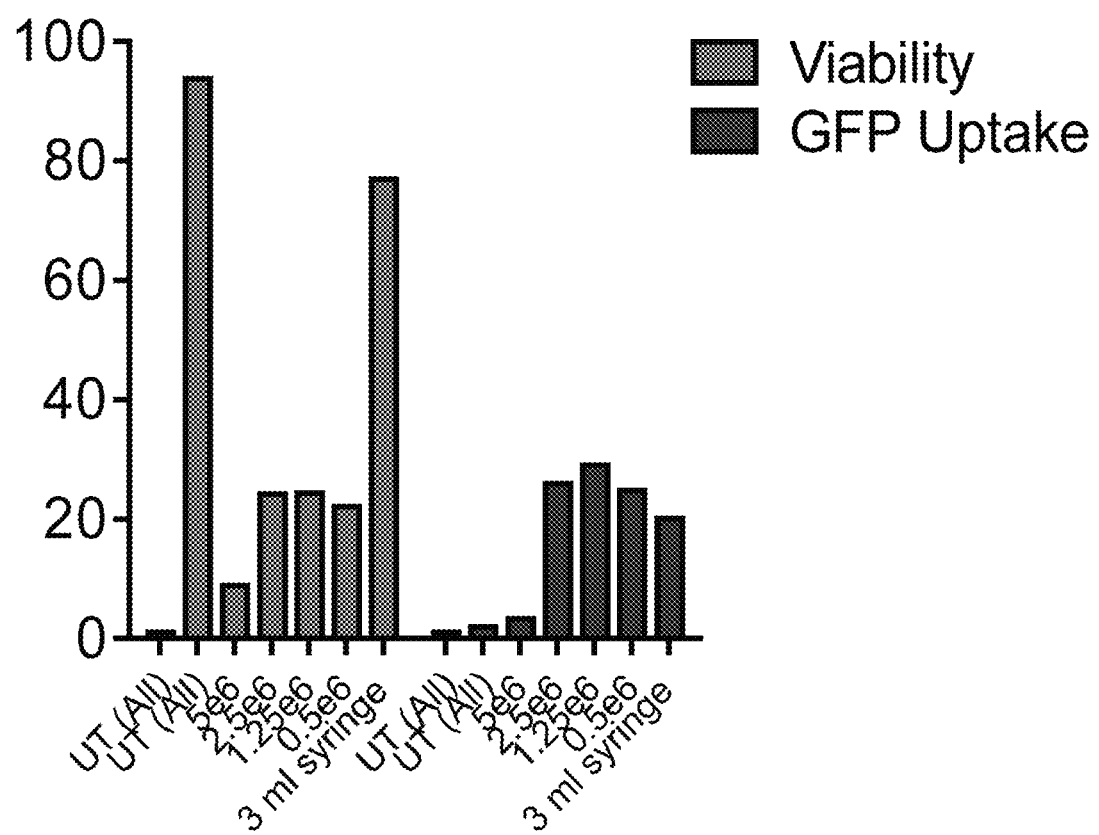
FIG. 13 illustrates experimental results using spray methods for payload delivery across cell membranes.

In a first exemplary implementation of the spray method using a 3 mL syringe 460, as illustrated in FIG. 11, cells ($2 \times 10^6$) resuspended in PBS were first mixed in a delivery solution containing a payload at a ratio of 1:1 in a 3 mL syringe 460 attached to an AriMist nebulizer 410 (Burgener Research, Inc., Mississauga, Ontario, Canada). The first exemplary implementation of the spray method can also include a precolumn coupler 420, a valve 430, a valve holder 440, and a Luer adapter 450. In implementations, the valve 430 and/or the valve holder 440 may be omitted. Cells and delivery solution were expelled through the nebulizer 410. The cells were dropletized into a 24-well plate and 150 µL of stop solution was applied after a 30 second incubation. After a further 30 second incubation, media (350 µL) was added. At the end of this spray test, the cells were incubated overnight at 37° C. and 5% $CO_2$ in a humidified incubator and assessed for green fluorescent protein (GFP) fluorescence by flow cytometry. GFP expression levels of 25%±5.0% in 1 donor and 2 experiments were achieved with a viability of 70% (FIG. 13).

A second exemplary implantation of the spray method using a liquid pump 530 manufactured by ELVEFLOW (Paris, France) (FIG. 12) was tested where cells were mixed in equal volume with delivery solution in a 1.5 mL Eppendorf tube. The tube was attached to the ELVEFLOW liquid pump through a pinch valve 520 and atomized through an AriMist nebulizer 510 into a 24-well plate. Stop solution was applied after a 30 second incubation followed by media addition.

The 3 mL syringe and the ELVEFLOW liquid pump configurations were tested using human T cells mixed with delivery solution prior to dropletizing through the AriMist nebulizer. Four cell concentrations were assessed using the ELVEFLOW system ($5 \times 10^6$, $2.5 \times 10^6$, $1.25 \times 10^6$ and $0.5 \times 10^6$). The 3 mL syringe setup used a total cell number of $2 \times 10^6$. Percentage GFP mRNA expression was measured using a BD Accuri C6 flow cytometer. 7-AAD was used to assess the viability. Cell debris was excluded from whole cells using forward and side scatter parameters. Single cells were selected by excluding doublets in the FSC height vs. FSC are plot in FIG. 13. GFP expression was analyzed on gated viable cells.

Example 3

Figure 15:
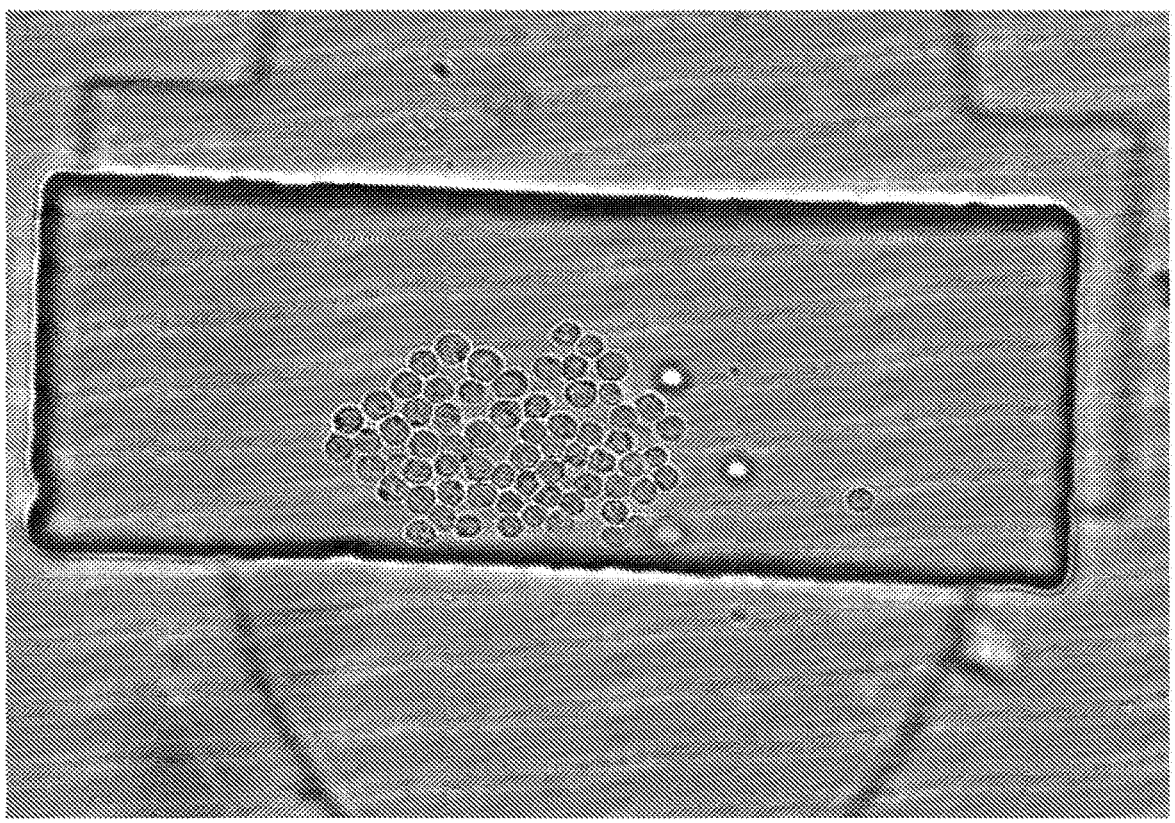
FIG. 15 is a brightfield image of cells that are captured in a trench-type process chamber during an experiment in an exemplary implementation of payload delivery across cell membranes using the trench-type process chamber.

In an embodiment, the payload delivery across the cell membranes can be implemented as a batch process using a trench-type process chamber. An example of the trench-type process chamber is illustrated FIG. 14, which is a microfluidic chip developed by the Dolomite Centre Ltd. With the trench-type process chamber, the cells are captured in the trenches in complete growth media. In some implementations, at least 20 individual cells are captured to analyze each of them. A brightfield image of the cells captured in the trenches is shown on FIG. 15. After the cells were captured, a background (e.g., reference) image was taken with brightfield and fluorescent filters. Subsequently, the complete growth media was removed from the reservoir and replaced with 50 μL of the delivery solution containing the payload. In operation, the media can be removed from the reservoir with a 200 μL pipette tip that feeds into the chip. After a set time, typically less than 3 minutes, the delivery solution was removed from the reservoir and replaced with 50 μL of stop solution. The cells were then imaged for the uptake of the payload. Further, live/dead stain was added to the reservoir after the cells had been exposed to the stop solution for about 15 minutes. The cells were imaged again for the uptake of a detectable marker such as FITC (fluorescein isothiocyanate) and PI (propidium iodide) to determine whether the cell membrane had been closed. Additionally, in another test, the payload was added to both the cell media and stop solution to extent the exposure and maximize the uptake of the payload. It was verified that this approach works for 2 μM DAPI (4',6-diamidino-2-phenylindole) with 35% ethanol.

Figure 16:
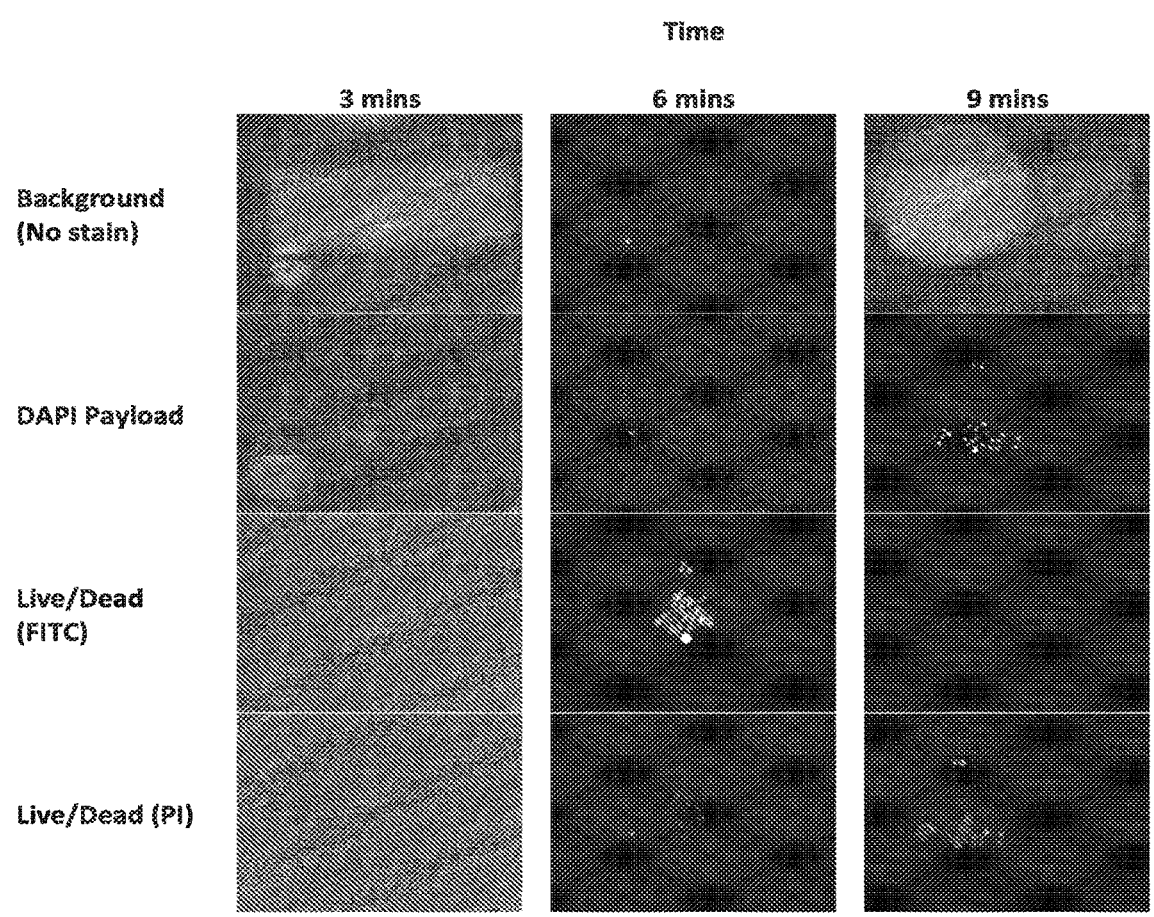
FIGS. 16 and 17 illustrate experiment results obtained in an exemplary implementation of payload delivery across cell membranes using a trench-type process chamber, showing an impact of the process time.
Figure 17:
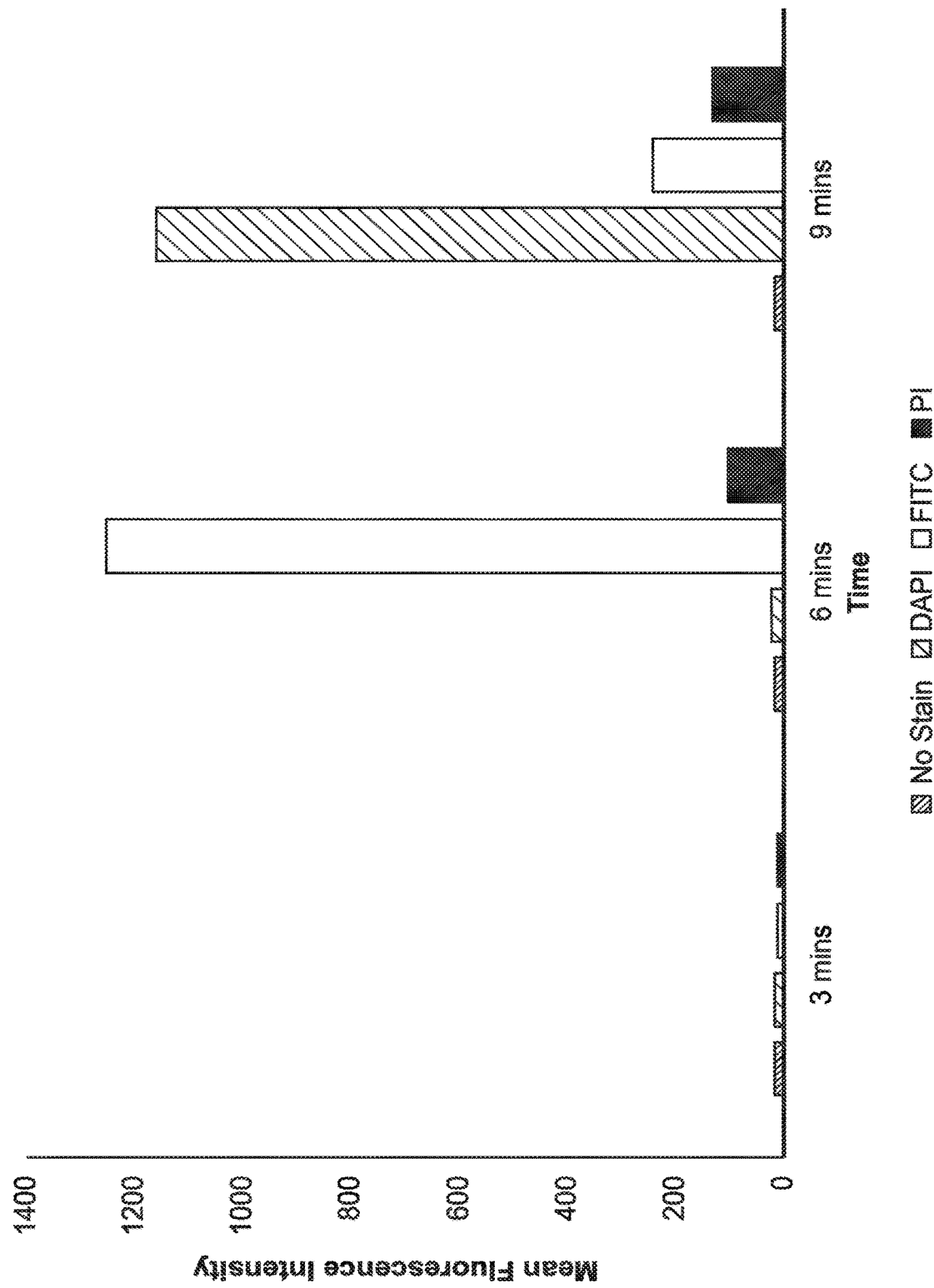
Figure 18:
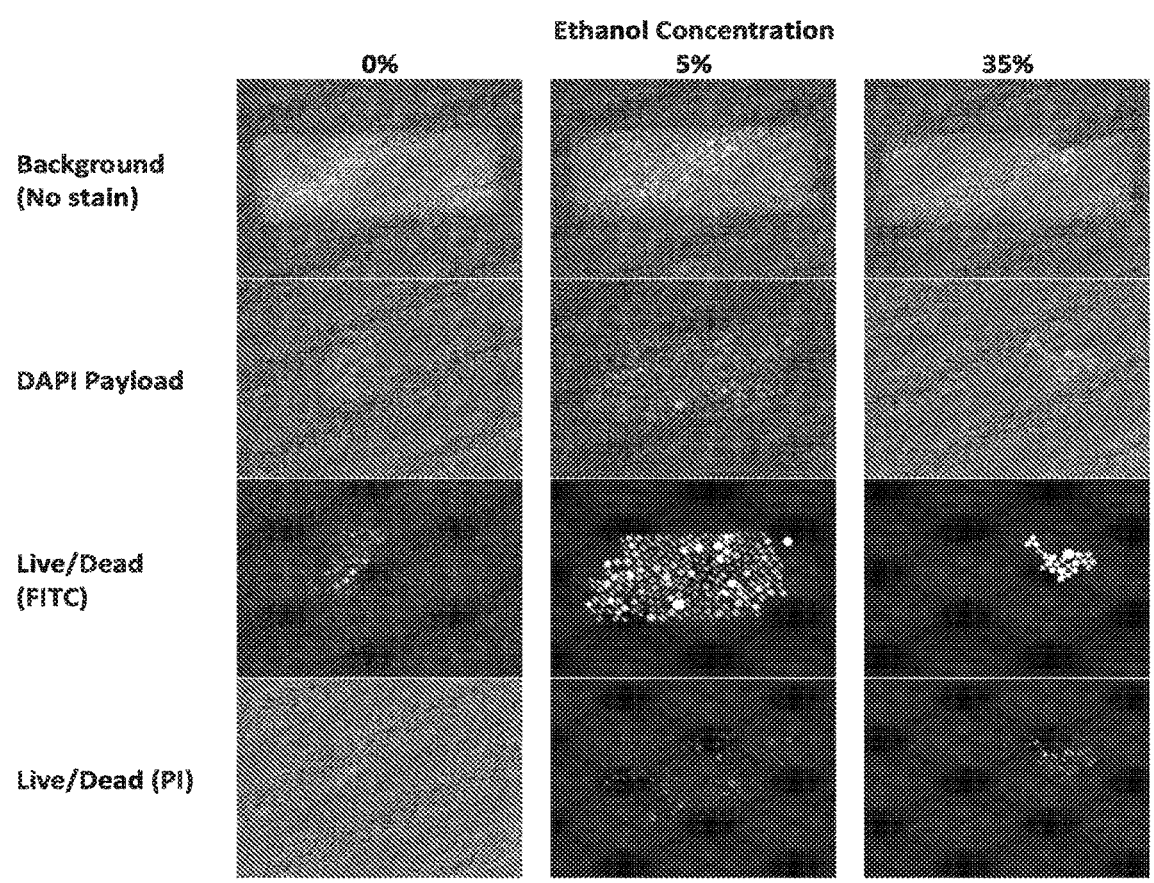
FIGS. 18 and 19 illustrate experiment results obtained in an exemplary implementation of payload delivery across cell membranes using a trench-type process chamber, showing an impact of the ethanol concentration.
Figure 19:
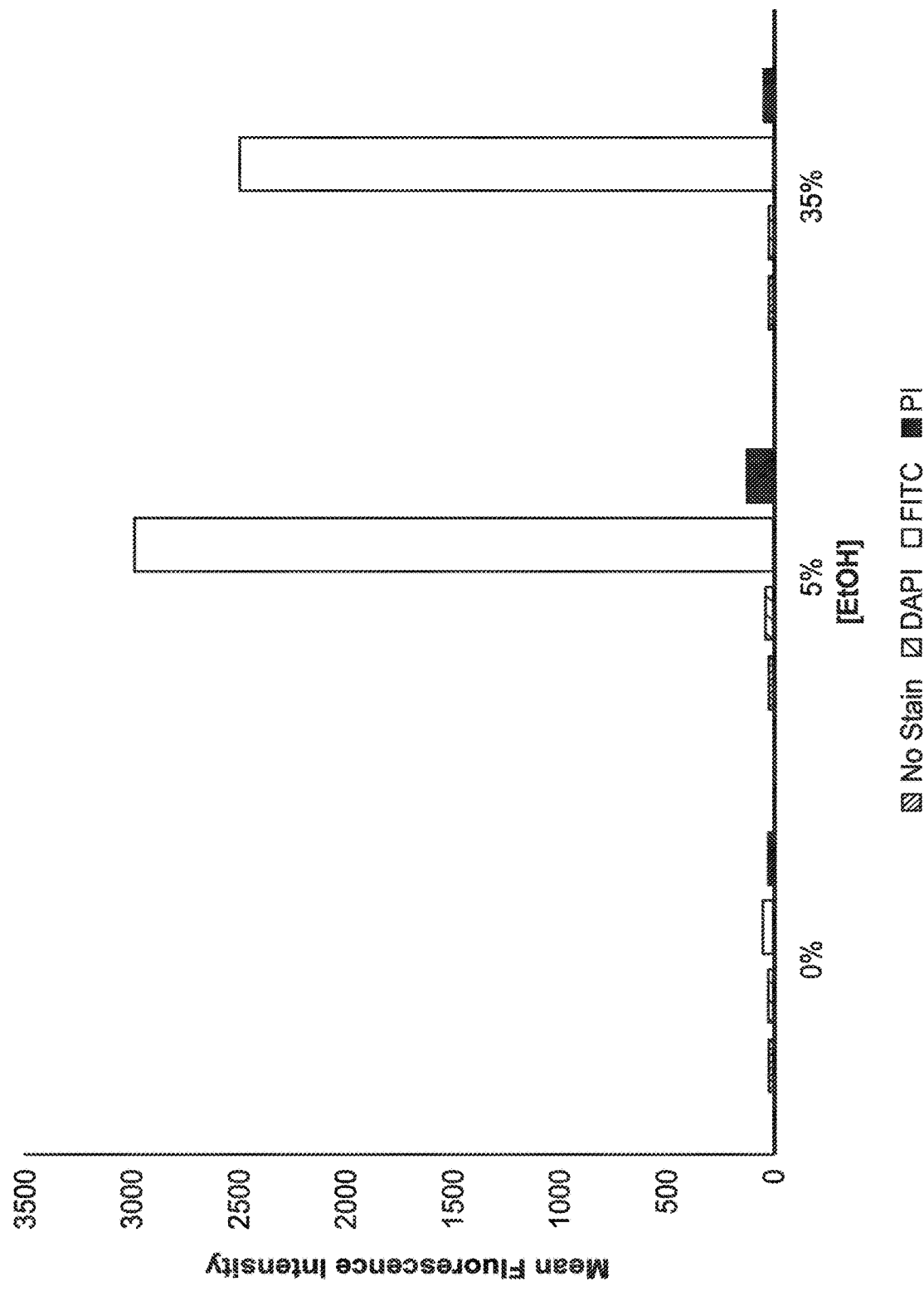
Figure 20:
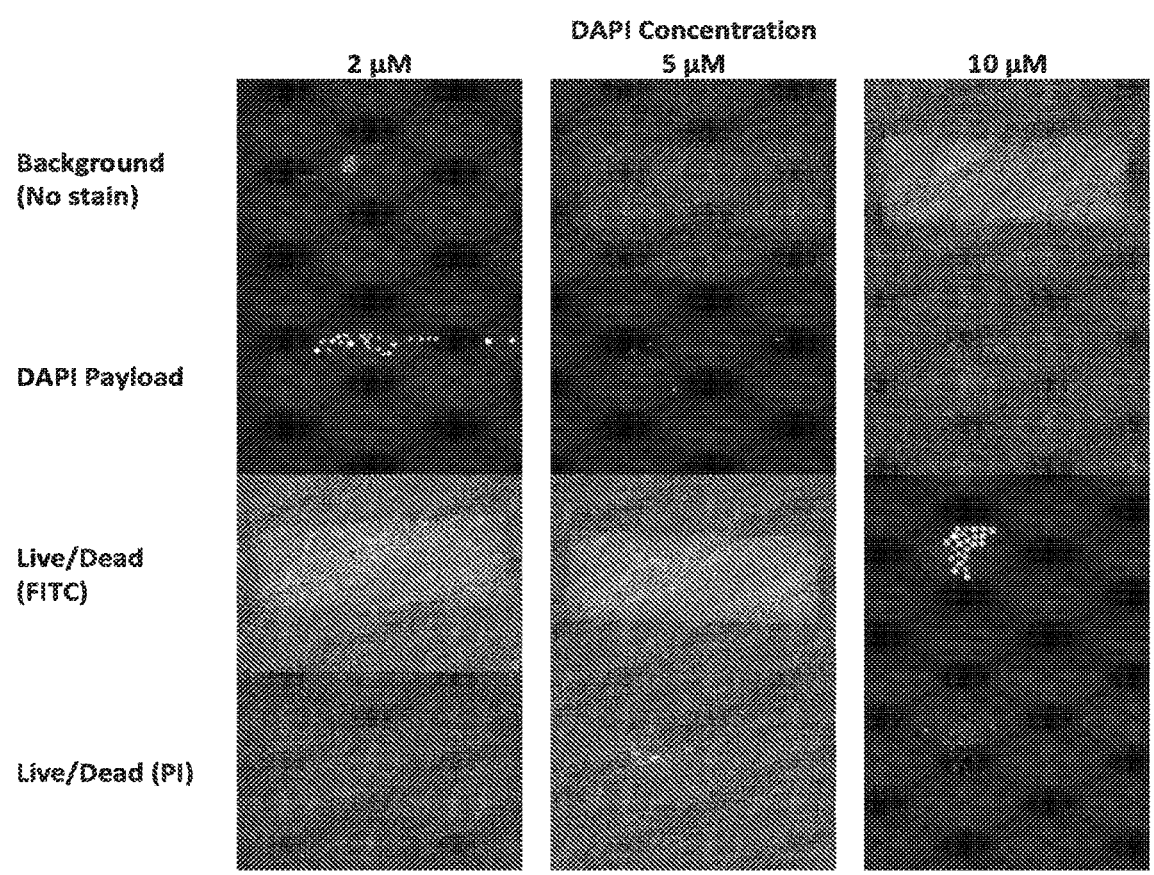
FIGS. 20 and 21 illustrate experiment results obtained in an exemplary implementation of payload delivery across cell membranes using a trench-type process chamber, showing an impact of the DAPI (4',6-diamidino-2-phenylindole) concentration.
Figure 21:
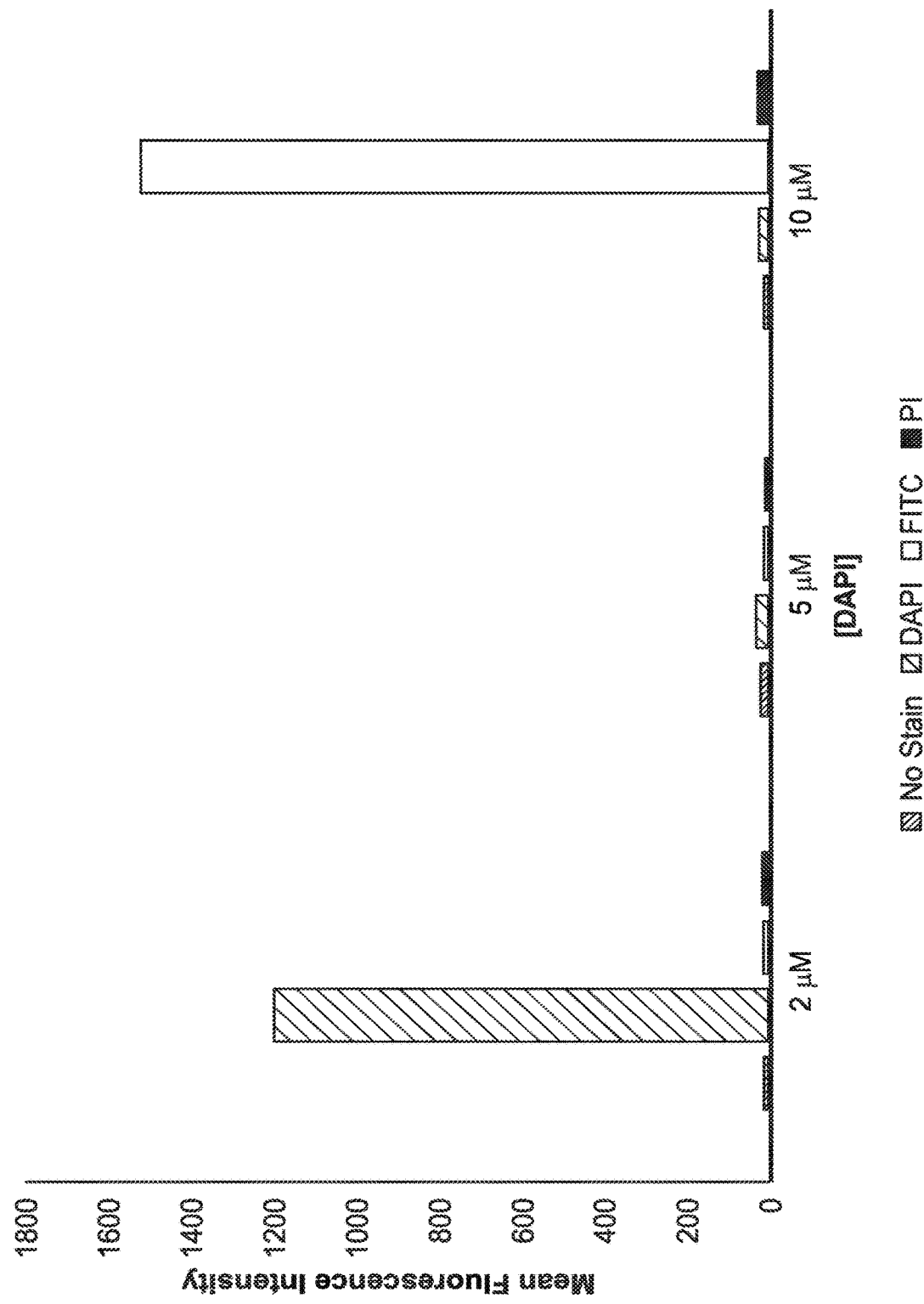

FIGS. 16-21 illustrate the results of the payload delivery experiment using an exemplary trench-type process chamber. In particular, FIGS. 16 and 17 show an impact of the delivery time. In this experiment, a DAPI concentration of 3 μM and an ethanol concentration of 25% were used while the delivery time was varied. It was shown that the payload uptake becomes the highest at 9 minute delivery time. However, reverse permeabilization was not achieved as the cells absorb PI. No PI was absorbed at 3 minute delivery time. FIGS. 18 and 19 show an impact of the ethanol centration. In this experiment, a DAPI concentration of 3 μM and a delivery time of 3 minutes were used while the ethanol concentration was varied. It was shown that the DAPI uptake was the highest with 35% ethanol concentration. FIGS. 20-21 show an impact of the DAPI concentration. In this experiment, an ethanol concentration of 35% and a deliver time of 3 minutes were used while the DAPI concentration was varied. It was shown that the highest uptake of DAPI payload and reverse permeabilization can be achieved with 2 μM DAPI concentration.

One skilled in the art will appreciate further features and advantages of the current subject matter based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of delivering a payload across a cell membrane, comprising:

mixing a population of cells in a suspension and a delivery payload in a delivery solution, the mixing performed using a substrate containing microfluidic channels, and the mixing occurring within at least one of the microfluidic channels,
wherein the population of cells includes a population of non-adherent cells, wherein the non-adherent cells comprise peripheral blood mononuclear cells (PBMCs), immune cells, or T lymphocytes,
wherein the delivery solution causes the population of cells to experience permeabilization and the delivery payload is delivered across membranes of the population of cells, and wherein the delivery solution includes an alcohol,
introducing a stop solution to the population of cells and the delivery payload subsequent to mixing the population of cells and the delivery payload such that the stop solution causes the population of cells to stop experiencing permeabilization; wherein at least a portion of the population of cells that stop experiencing permeabilization are viable, and
analyzing the at least a portion of the population of cells that stop experiencing permeabilization and are viable.

2. The method of claim 1, wherein the population of cells includes T cells and the delivery payload includes mRNA.

3. The method of claim 1, wherein the suspension and the delivery solution experience a first mixing cascade and a second mixing cascade.

4. The method of claim 1, wherein mixing the population of cells and the delivery payload includes pumping the population of cells and the delivery payload into a microfluidic mixing chip.

5. The method of claim 4, wherein a narrowest channel of the microfluidic mixing chip is at least 5 times larger than diameters of the population of cells.

6. The method of claim 1, wherein the population of cells and the delivery payload experience laminar flows.

7. The method of claim 1, further comprising mixing at least one additive with the population of cells in the suspension and the delivery payload in the delivery solution.

8. The method of claim 1, wherein the delivery solution includes an isotonic aqueous solution, the aqueous solution including the payload and an alcohol at greater than 5 percent (v/v) concentration.

9. The method of claim 8, wherein said alcohol comprises ethanol.

10. The method of claim 8, wherein said aqueous solution comprises greater than 10% ethanol.

11. The method of claim 8, wherein said aqueous solution comprises between 20-30% ethanol.

12. The method of claim 8, wherein said aqueous solution comprises 27% ethanol.

13. The method of claim 8, wherein said aqueous solution comprises between 12.5-500 mM KCl.

14. The method of claim 8, wherein said aqueous solution comprises 106 mM KCl.

15. The method of claim 8, wherein said payload comprises a messenger ribonucleic acid (mRNA).

16. The method of claim 15, wherein said mRNA encodes a gene-editing composition.

17. The method of claim 16, wherein said gene editing composition reduces the expression of PD-1.

18. The method of claim 15, wherein said mRNA encodes a chimeric antigen receptor.

19. The method of claim 1 for use to deliver a cargo compound or composition to a mammalian cell.

20. The method of claim 1, wherein the microfluidic channel includes a channel width between 0.01 μm and 100 μm.

21. The device of claim 1, wherein the microfluidic channel includes a channel width between 100 μm and 1 mm.

22. The device of claim 1, wherein the microfluidic channel includes a channel width greater than or equal to 1 mm.

23. The method of claim 1, wherein greater than about 70% of the cells remain viable after introducing the stop solution.

\* \* \* \* \*